(12) United States Patent
Tung et al.

(10) Patent No.: US 9,463,432 B2
(45) Date of Patent: Oct. 11, 2016

(54) INTEGRATED PROCESS AND METHODS OF PRODUCING (E)-1-CHLORO-3,3,3-TRIFLUOROPROPENE

(71) Applicant: Honeywell International Inc., Morristown, NJ (US)

(72) Inventors: Hsueh Sung Tung, Getzville, NY (US); Konstantin A. Pokrovski, Orchard Park, NY (US); Daniel C. Merkel, West Seneca, NY (US); Robert Johnson, Lancaster, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/697,788

(22) Filed: Apr. 28, 2015

(65) Prior Publication Data

US 2015/0224470 A1    Aug. 13, 2015

Related U.S. Application Data

(62) Division of application No. 13/019,823, filed on Feb. 2, 2011, now Pat. No. 9,045,386.

(60) Provisional application No. 61/379,633, filed on Sep. 2, 2010, provisional application No. 61/305,803, filed on Feb. 18, 2010.

(51) Int. Cl.
| | |
|---|---|
| C07C 17/20 | (2006.01) |
| B01J 19/24 | (2006.01) |
| C07C 17/25 | (2006.01) |
| C07C 17/358 | (2006.01) |
| C07C 17/383 | (2006.01) |
| B01J 23/26 | (2006.01) |
| B01J 37/26 | (2006.01) |

(52) U.S. Cl.
CPC .......... B01J 19/245 (2013.01); C07C 17/206 (2013.01); C07C 17/25 (2013.01); C07C 17/358 (2013.01); C07C 17/383 (2013.01); B01J 23/26 (2013.01); B01J 37/26 (2013.01); B01J 2219/00006 (2013.01); B01J 2219/24 (2013.01); C07B 2200/09 (2013.01); Y02P 20/582 (2015.11)

(58) Field of Classification Search
None
See application file for complete search history.

(56) References Cited

U.S. PATENT DOCUMENTS

| | | | |
|---|---|---|---|
| 5,608,126 A | 3/1997 | Morikawa et al. | |
| 5,710,352 A | 1/1998 | Tung | |
| 6,235,951 B1 | 5/2001 | Sakyu et al. | |
| 6,844,475 B1 | 1/2005 | Tung et al. | |

(Continued)

FOREIGN PATENT DOCUMENTS

| | | |
|---|---|---|
| EP | 0611744 A1 | 8/1994 |
| EP | 0729932 A1 | 9/1996 |

(Continued)

OTHER PUBLICATIONS

Morrison et al., "Azeotropy in Refridgerant Mixtures", International Journal of Refrigeration, 1993, vol. 16, No. 2, pp. 129-138.

(Continued)

*Primary Examiner* — Clinton Brooks
(74) *Attorney, Agent, or Firm* — Bruce O. Bradford

(57) ABSTRACT

The present invention relates to methods, process, and integrated systems for economically producing (E)-1-chloro-3,3,3-trifluoropropene via vapor phase and/or liquid processes.

2 Claims, 8 Drawing Sheets

(56) References Cited

U.S. PATENT DOCUMENTS

| | | |
|---|---|---|
| 8,426,656 B2 | 4/2013 | Merkel et al. |
| 8,648,221 B2 | 2/2014 | Merkel et al. |
| 2008/0103342 A1 | 5/2008 | Wang et al. |
| 2010/0237279 A1 | 9/2010 | Hulse et al. |
| 2012/0059199 A1 | 3/2012 | Pokrovski et al. |

FOREIGN PATENT DOCUMENTS

| | | |
|---|---|---|
| EP | 0877009 A1 | 11/1998 |
| WO | 9504022 A1 | 2/1995 |
| WO | 9724307 A1 | 7/1997 |
| WO | 9812161 A1 | 3/1998 |
| WO | 9821171 A1 | 5/1998 |
| WO | 20100059496 A1 | 5/2010 |

OTHER PUBLICATIONS

Kim et al, "A Study to Determine the Existence of an Azeotropic R-22 "Drop-In" Substitute", Prepared by U.S. Department of Commerce for Electric Power Research Institute, Mar. 1996, pp. 1-45.

European Supplemental Search Report issued in 11745076.7, dated Aug. 21, 2003.

INTEGRATED PROCESS AND METHODS OF PRODUCING (E)-1-CHLORO-3,3,3-TRIFLUOROPROPENE

CROSS REFERENCE TO RELATED APPLICATIONS

This application is related to a divisional filing from commonly owned U.S. application Ser. No. 13/019,823, filed Feb. 2, 2011, now U.S. Pat. No. 9,045,386. The '823 application claims the priority benefit of U.S. provisional application No. 61/305,803, filed Feb. 18, 2010 and U.S. provisional application No. 61/379,633, filed Sep. 2, 2010. The contents of these applications are hereby incorporated herein by reference.

FIELD OF THE INVENTION

This invention relates to processes, methods and systems for producing hydrochlorofluorooleins, particularly (E) 1-chloro-3,3,3-trifluoropropene.

BACKGROUND OF THE INVENTION

Chlorofluorocarbon (CFC) based chemicals have been widely use in industry in a variety of different applications including as refrigerants, aerosol propellants, blowing agents and solvents, among others. Certain CFCs, however, are suspected of depleting the Earth's ozone layer. Accordingly, more environmentally friendly substitutes have been introduced as replacements for CFCs. One example of such a substitute is 1,1,1,3,3-pentafluoropropane (HFC-245fa). HFC-245fa is recognized as having favorable physical properties for certain industrial applications, such as foam blowing agents and solvents, and therefore is considered to be a good substitute for the CFCs previously used for these applications. Unfortunately, the use of certain hydrofluorocarbons, including HFC-245fa, in industrial applications is now believed to contribute to global warming. As a result, more environmentally friendly substitutes for hydrofluorocarbons are now being sought.

The compound 1-chloro-3,3,3-trifluoropropene, also know as HCFO-1233zd or simply 1233zd, is a leading candidate for replacing HFC-245fa in some applications, including blowing agents and solvents. 1233zd has a Z-isomer and an E-isomer. Due to differences in the physical properties between these two diastereoisomers, pure 1233zd (E), pure 1233zd(Z), or certain mixtures of the two isomers may be suitable for particular applications as refrigerants, propellants, blowing agents, solvents, or for other uses.

Processes for synthesizing 1233zd are known. WO 97/24307, for example, discloses a process for preparing 1233zd via the gas-phase reaction of 1,1,1,3,3-pentachloropropane (HCC-240fa) with hydrogen fluoride (HF). This process, however, produces relatively low yields of 1233zd. U.S. Pat. No. 6,844,475 describes a liquid phase reaction of HCC-240fa with HF to produce 1233zd in higher yields. A preferred temperature range for this reaction was purported to be about 50° C. to about 120° C., with specific examples being demonstrated at 90° C. (resulting in a 1233zd yield of about 80 wt. %) and 120° C. (resulting in a 1233zd yield of over 90 wt. %). The 1233zd yield at the lower temperature is not particularly good. The yield at the higher temperature is good, but Applicants have found that operating the process at this temperature and above produces increased amounts of the Z-isomer. Accordingly, there remains a need for a process for selectively producing 1233zd(E) in high yields. This application satisfies that need among others.

SUMMARY OF THE INVENTION

Applicants have unexpectedly found that a 1233zd reaction product having a majority of E-isomer is formed by carefully maintaining the temperature of either (1) a catalytic liquid phase reaction between HF and one or a combination of HCC-240fa, 1,1,3,3-tetrachloropropene and/or 1,3,3,3-tetrachloropropene or (2) a catalytic vapor phase reaction between HCC-240fa and HF. With respect to the former, the temperature is maintained preferably, though not exclusively, at about 85° C. to about 120° C. Applicants have also discovered that the E-isomer yield is further improved by passing the liquid phase product through a stripping column as it leaves the reactor to reflux unreacted reactants back to the reactor, particularly, though not exclusively, when the stripping column is operated to achieve an average stripping temperature of about 10° C. to about 40° C. below the corresponding reaction temperature. With respect to the gas phase reaction, the temperature is maintained preferably, though not exclusively, at about 200 to about 450° C., with a pressure being maintained at about 0 to about 160 psig.

Overall process efficiency is achieved by integrating other unit operations to separate and recycle unreacted reactants and/or undesirable isomers of 1233zd, and also to separate and remove by-products. Thus, in certain preferred embodiments, the process is directed to an integrated process for producing 1233zd(E) in high yields.

In one aspect, the instant invention relates to a method or process for producing a chlorofluoroalkene comprising: (a) providing a liquid reaction admixture comprising hydrogen fluoride, 1,1,1,3,3-pentachloropropane (or a hydrohalocarbon mixture of 1,1,1,3,3-pentachloropropane and/or 1,1,3,3-tetrachloropropene and/or 1,3,3,3-tetrachloropropene), and a fluorinated metal chloride catalyst, wherein said hydrogen fluoride and 1,1,1,3,3-pentachloropropane (or the hydrohalocarbon mixture) are present in a molar ratio of greater than about 3:1 and wherein said a fluorinated metal chloride catalyst is selected from the group consisting of partially or fully fluorinated $TiCl_4$, $SnCl_4$, $TaCl_5$, $SbCl_3$, $FeCl_3$, or $AlCl_3$; and (b) reacting said hydrogen fluoride and 1,1,1,3,3-pentachloropropane (or the hydrohalocarbon mixture of 1,1,1,3,3-pentachloropropane and/or 1,1,3,3-tetrachloropropene and/or 1,3,3,3-tetrachloropropene) in the presence of said catalyst in a liquid phase and at a reaction temperature of about 85° C. to about 120° C. to produce a reaction product stream comprising (E)1-chloro-3,3,3-trifluoropropene, hydrogen chloride, unreacted hydrogen fluoride, entrained catalyst, (Z)1-chloro-3,3,3-trifluoropropene and, optionally, unreacted hydrohalocarbon starting product (e.g. 1,1,1,3,3-pentachloropropane, and/or 1,1,3,3-tetrachloropropene and/or 1,3,3,3-tetrachloropropene), wherein said product stream has a weight ratio of (E)1-chloro-3,3,3-trifluoropropene to (Z)1-chloro-3,3,3-trifluoropropene of greater than 1.

This method or process may further include the step of (c) contacting said reaction product stream with a heat exchanger to produce (i) a first crude product stream comprising a majority of said hydrogen chloride, a majority of said (E)1-chloro-3,3,3-trifluoropropene, optionally a majority of said (Z)1-chloro-3,3,3-trifluoropropene, and at least a portion of said unreacted hydrogen fluoride, wherein said portion is an amount sufficient to form an azeotrope with one or more of said (E)1-chloro-3,3,3-trifluoropropene and said (Z)1-chloro-3,3,3-trifluoropropene, and (ii) a reflux component comprising a majority of said entrained catalyst and said unreacted hydrogen fluoride; and (d) returning said reflux component to said reaction admixture.

In further embodiments, the method or process further includes one or more of the following steps: (e) separating unreacted reactants, including unreacted 1,1,1,3,3-pentachloropropane, and/or 1,1,3,3-tetrachloropropene and/or 1,3,3,3-tetrachloropropene, via distillation and recycling these unreacted reactants back to the reactor; (f) removing at least a portion, and preferably a majority, of hydrochloric acid by-product; (g) separating and recycling unreacted HF in a crude product stream via a sulfuric acid adsorption or a phase separation; (h) distillation of the crude product stream to separate (E)1233zd from reaction by-products; and (i) isomerization of 1233zd(Z) by-products to form 1233zd(E).

The foregoing steps may be provided as an integrated system for producing a hydrofluoroolefin comprising (a) one or more feed streams cumulatively comprising hydrogen fluoride and 1,1,1,3,3-pentachloropropane (or a hydrohalocarbon mixture of 1,1,1,3,3-pentachloropropane, and/or 1,1,3,3-tetiachloropropene and/or 1,3,3,3-tetrachloropropene); (b) a liquid phase reactor charged with a liquid phase fluorination catalyst and maintained at a first temperature of about 85° C. to about 120° C., wherein said liquid phase reactor is fluidly connected to said one or more feed streams; (c) a stripping system comprising a stripping column having an average temperature maintained at a second temperature of about 10° C. to about 40° C. below said first temperature, a reflux stream fluidly connected to said stripping column, and a first crude product stream fluidly connected to said stripping column, wherein said reflux stream is fluidly connected to said liquid phase reactor; (d) a hydrogen chloride removal system comprising a first distillation column, a hydrogen chloride by-product stream fluidly connected to said first distillation column, and a second crude product stream fluidly connected to said first distillation column, wherein said first distillation column is fluidly connected to said stripping column; (e) a hydrogen fluoride recovery system comprising a sulfuric acid absorption and recycle system or a phase separation vessel, a second recycle stream comprising hydrogen fluoride fluidly connected to said sulfuric acid absorption and recycle system or a phase separation vessel, a third product stream comprising (E) and (Z) 1-chloro-3,3,3-trifluoropropene fluidly connected to said sulfuric acid absorption and recycle system or a phase separation vessel, wherein said sulfuric acid absorption and recycle system or a phase separation vessel is fluidly connected to said second crude product stream; and (f) a 1-chloro-3,3,3-trifluoropropene purification system comprising a second distillation column fluidly connected to said third product stream; a final product stream comprising (E)1-chloro-3,3,3-trifluoropropene fluidly connected to said second distillation column; a second by-product stream fluidly connected to said distillation column, a isomerization reactor fluidly connected to said second by-product stream; an a product recycle stream fluidly connected to said isomerization reactor and said second distillation column.

In another embodiment, the instant invention relates to a method or process for preparing (E)1-chloro-3,3,3-trifluoropropene by first providing 1,1,1,3,3-pentachloropropane with hydrogen fluoride in a vapor phase reaction mixture and in the presence of a fluorinated catalyst. The mixture is provided within a reactor where hydrogen fluoride and 1,1,1,3,3-pentachloropropane are present in a HF:organic molar ratio of greater than about 3:1. 1,1,1,3,3-pentachloropropane is reacted with hydrogen fluoride in the presence of the catalyst and at a reaction temperature of about 200 to about 450° C. and a pressure of about 0 to about 160 psig. The resulting product stream includes (E)1-chloro-3,3,3-trifluoropropene, hydrogen chloride, unreacted hydrogen fluoride, unreacted 1,1,1,3,3-pentachloropropane, reaction by-products, and optionally (Z)1-chloro-3,3,3-tifluoropropene.

The fluorinated catalyst for the vapor phase reaction may be selected from one or more catalysts in the group of chromium based catalysts, aluminum based catalysts, cobalt based catalysts, manganese based catalysts, nickel and iron oxide based catalysts, hydroxide based catalysts, halide based catalysts, oxyhalide based catalysts, inorganic salts thereof or mixtures thereof. In one embodiment, the catalyst is selected from $Cr_2O_3$, $Cr_2O_3/Al_2O_3$, $Cr_2O_3/AlF_3$, $Cr_2O_3/$carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. In other embodiments, the catalyst is selected from $FeCl_3/C$, $SnCl_4/C$, $TaCl_5/C$, $SbCl_3/C$, $AlCl_3/C$, and $AlF_3/C$.

The product or final reaction stream in the vapor phase reaction may undergo post-reaction processing to isolate the desired products and recycle certain unreacted starting reagents. In one embodiment, such a process step includes separating the reaction product stream to produce (a) a first overhead stream of HCl, and (b) a first bottoms stream including unreacted hydrogen fluoride, unreacted 1,1,1,3,3-pentachloropropane, (E)1-chloro-3,3,3-trifluoropropene, and optionally (Z)1-chloro-3,3,3-trifluoropropene. The first bottoms stream may then be separated to produce (a) a recycle stream of HF, which may be recycled back to the vapor phase reaction; and (b) a stream that includes unreacted 1,1,1,3,3-pentachloropropane, reaction by-products, (E)1-chloro-3,3,3-trifluoropropene, and optionally (Z)1-chloro-3,3,3-trifluoropropene. This stream can be then separated further to produce (a) a stream of unreacted 1,1,1,3,3-pentachloropropane and reaction by-products; and (b) a stream comprising (E)1-chloro-3,3,3-trifluoropropene, and optionally (Z)1-chloro-3,3,3-trifluoropropene. In embodiments where both the E and Z isomer are provided, the components of said stream are then separated, i.e., (E)1-chloro-3,3,3-trifluoropropene is separated from (Z)1-chloro-3,3,3-trifluoropropene. The (Z)1-chloro-3,3,3-thfluoropropene may then be isomerized to produce (E)1-chloro-3,3,3-trifluoropropene. In any of the foregoing steps the separation technique includes, but is not limited to, distillation or adsorption, but may also be adapted to use alternative separation techniques that are known in the art.

The foregoing steps for the vapor phase reaction may be provided in an integrated system for producing a hydrofluoroolefin including (a) one or more feed streams cumulatively of hydrogen fluoride and 1,1,1,3,3-pentachloropropane; (b) a vapor phase reactor with a vapor phase fluorination catalyst and maintained at a first temperature of about 200 to about 450° C. and a pressure of about 0 to about 160 psig, wherein said vapor phase reactor is fluidly connected to said one or more feed streams; (c) a hydrogen chloride removal system including a first distillation column, a hydrogen chloride by-product stream fluidly connected to said first distillation column, and a crude product stream fluidly connected to said first distillation column wherein said first distillation column is fluidly connected to said vapor phase reactor; (d) a hydrogen fluoride recovery system including a sulfuric acid stripping and recycle system or a phase separation vessel, a recycle stream comprising hydrogen fluoride fluidly connected to said sulfuric acid stripping and recycle system or a phase separation vessel, a product stream including (E) and (Z) 1-chloro-3,3,3-trifluoropropene fluidly connected to said sulfuric acid stripping and recycle system or a phase separation vessel, wherein said sulfuric acid stripping and recycle system or a phase separation vessel is fluidly connected to said crude product stream; (e) a 1-chloro-3,3,3-trifluoropropene purification system including a second distillation column fluidly connected to said product stream; a final product stream including (E) 1-chloro-3,3,3-trifluoropropene fluidly connected to said second distillation column; a second by-product stream fluidly connected to said distillation column, a isomerization reactor fluidly connected to said second by-product stream; and a product recycle stream fluidly connected to said isomerization reactor and said second distillation column.

Additional embodiments and advantages to the instant invention will be readily apparent to one of skill in the art based on the disclosure provided below.

DETAILED DESCRIPTION OP PREFERRED EMBODIMENTS OF THE INVENTION

Figure 1:
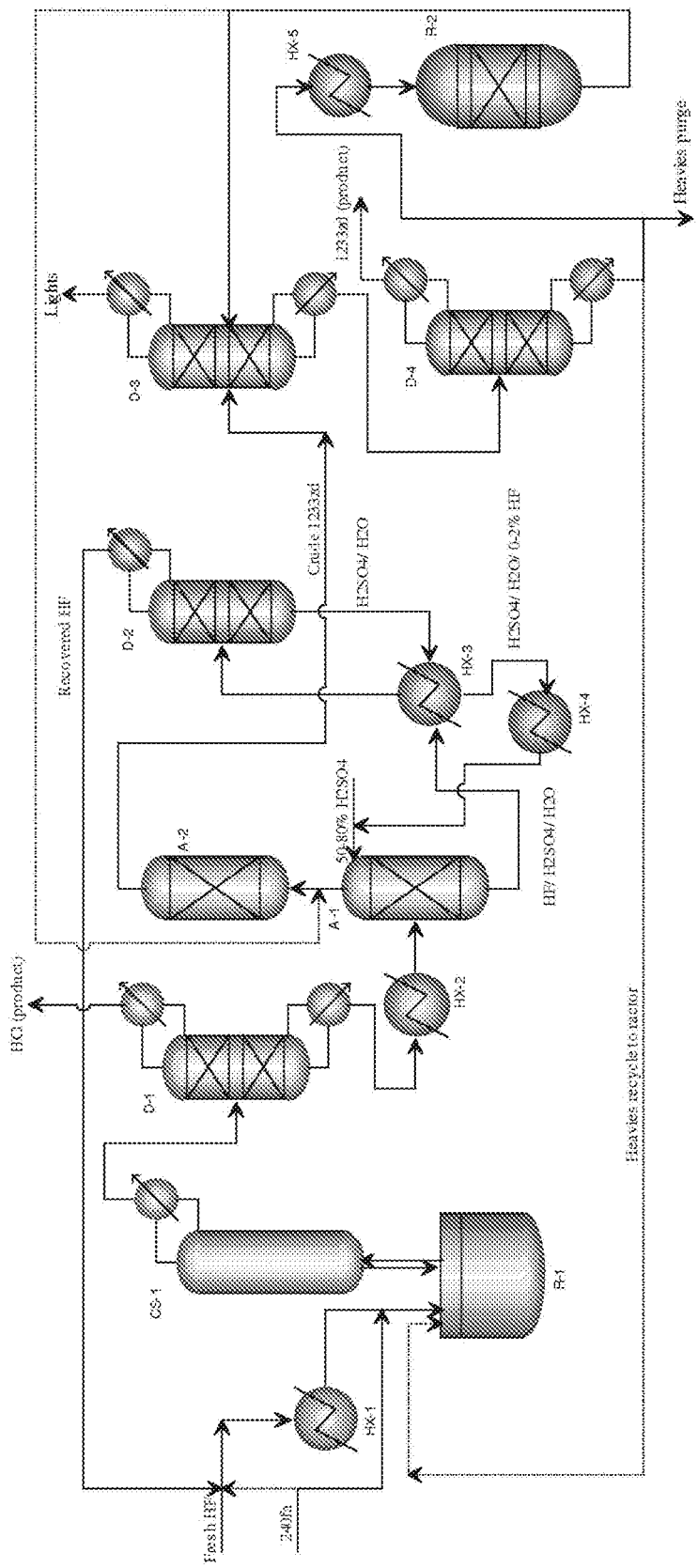
FIG. 1 shows a schematic depiction of an integrated liquid phase synthesis of 1233zd (E) according to a preferred embodiment of the invention.

In certain embodiments, the present invention relates to methods and process for continuously and economically producing (E)-1-chloro-3,3,3-trifluoropropene via a fully integrated liquid phase or vapor phase process. Representative fully integrated processes for making (E)-1-chloro-3,3,3-trifluoropropene are described below.

Liquid Phase Reaction

The reaction chemistry for the liquid phase process involves a single-step reaction of 1,1,1,3,3-pentachloropropane (or a hydrohalocarbon mixture of 1,1,1,3,3-pentachloropropane and/or 1,1,3,3-tetrachloropropene and/or 1,3,3,3-tetrachloropropene) with anhydrous HF in a liquid-phase, catalyzed reactor to produce primarily (E)-1-chloro-3,3,3-trifluoropropene (1233zd(E)) plus HCl as a by-product. Preferably, the reaction is maintained under conditions (temperature, pressure, residence time) to increase the relative ratio of (E) to (Z) isomers of 1233zd while also minimizing the reaction of HF with the resulting 1233zd(E) which would lead to the formation of HFC-244fa, which in turn can react further to produce HFO-1234ze. Accordingly, the desired reactions involve:

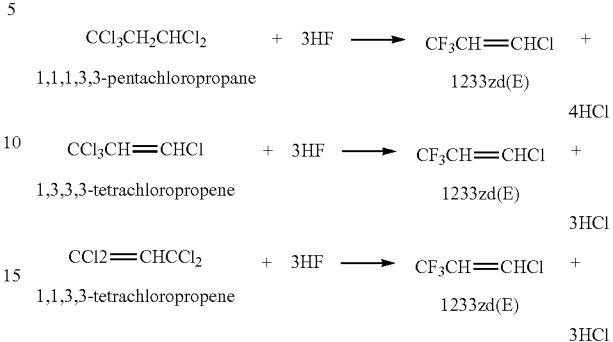

Undesired reactions, which are preferably avoided, include:

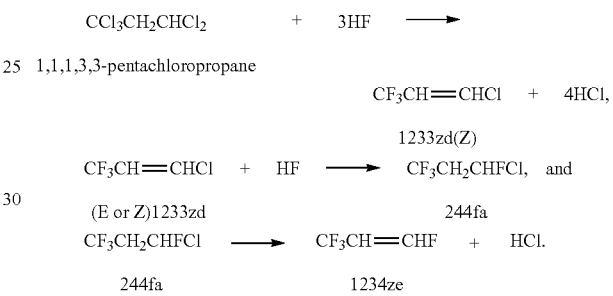

In certain embodiments, the manufacturing process for the liquid phase reaction comprises six major unit operations: (1) catalyst preparation (preferably titanium tetrachloride), (2) fluorination reaction (continuous or semi-batch mode) using HF with simultaneous removal of by-product HCl and the product 1233zd (E), (3) separation and purification of by-product HCl, (4) separation of excess HF back to (2), (5) purification of final product, 1233zd (E), and (6) isomerization of by-product 1233zd (Z) to 1233zd(E) to maximize the process yield. The relative positions of these operations are shown in FIGS. 1-4.

Unit Operation One: Catalyst Preparation

In one aspect, the fluorination reaction described herein uses a liquid phase catalyst of proper strength to achieve the desired reaction preferentially. One fluorination catalyst used is titanium tetrachloride (liquid under ambient conditions) which has been partially or totally fluorinated by the action of anhydrous HF. This catalyst unexpectedly achieves the desired degree of conversion without forming a significant amount of undesired volatile by-products (although formation of a moderate amount of HCl is unavoidable). The catalyst fluorination is conducted by adding a specified amount of HF and fluorination catalyst to a reaction vessel equipped with an agitator at a temperature in the range of 0-120° C. Optionally, catalyst fluorination can be conducted by combining HF, fluorination catalyst, and 1,1,1,3,3-pentachloropropane or 1,1,1,3,3-pentachloropropane and/or 1,1,3,3-tetrachloropropene and/or 1,3,3,3-tetrachloropropene mixture in the reactor provided the reactor temperature is below the 1,1,1,3,3-pentachloropropane or 1,1,1,3,3-pentachloropropane and/or 1,1,3,3-tetrachloropropene and/or 1,3,3,3-tetrachloropropene mixture fluorination reaction initiation temperature (<85° C.) for safety considerations. Order of fluorination catalyst, HF, and/or 1,1,1,3,3-pentachloropropane or 1,1,1,3,3-pentachloropropane and/or 1,1, 3,3-tetrachloropropene and/or 1,3,3,3-tetrachloropropene mixture addition to reactor is not important, but addition of HF first is preferred. Partial or complete fluorination of the catalyst will occur upon addition and HCl by-product will be generated increasing the pressure within the reaction vessel which is then controlled at the desired reaction pressure. Additional fluorination catalysts that can be used include $SnCl_4$, $TaCl_5$, $SbCl_3$, $FeCl_3$, and $AlCl_3$ which have been partially or totally fluorinated by the action of anhydrous HF. Preferably the reactor is constructed from materials which are resistant to the corrosive effects of the HF and catalyst, such as Hastelloy-C, Inconel, Monel, Incalloy, or fluoropolymer-lined steel vessels. Such liquid-phase fluorination reactors are well known in the art.

Unit Operation Two: Fluorination Reaction and Reactor and Stripping Column.

The arrangement and operation of the reactor and stripping column is particularly important in achieving a high yield of 1233zd(E). In a preferred embodiment, the reaction is conducted of an agitated, temperature-controlled reactor containing the liquid fluorination catalyst. One or more feeds comprising hydrogen fluoride and 1,1,1,3,3-pentachloropropane or 1,1,1,3,3-pentachloropropane and/or 1,1,3,3-tetrachloropropene and/or 1,3,3,3-tetrachloropropene mixture enter the reactor where they contact each other and the catalyst in a liquid phase. The resulting reaction produces a gas phase product comprising 1233zd(E) as well as various other by-products including HCl and possibly 1233zd (Z). The gas phase product leaves the liquid phase reactor and enters an integrated distillation column (operating in stripping mode) which permits the desired product to leave (along with by-product HCl, traces of light organics [principally 1234ze(E+Z)], and sufficient anhydrous hydrogen fluoride (AHF) to form the azeotropes), while retaining the bulk of the HF, plus under-fluorinated and dimerized organics, plus fluorination catalyst entrained in the gas stream. Once the catalyst has been prepared, the reaction can be initiated immediately upon heating to the desired reaction temperature. The flow of HF needed for the catalyst preparation can be resumed, and addition of the 1,1,1,3,3-pentachloropropane or 1,1,1,3,3-pentachloropropane and/or 1,1, 3,3-tetrachloropropene and/or 1,3,3,3-tetrachloropropene mixture can be started immediately to cause continuous, reaction. Alternatively, a large amount of the same 1,1,1,3, 3-pentachloropropane or 1,1,1,3,3-pentachloropropane and/ or 1,1,3,3-tetrachloropropene and/or 1,3,3,3-tetrachloropropene mixture can be added at one time as a batch charge, and then HF can be added gradually to the reactor (a semi-batch operation). Alternatively, a large amount of HF can be added at one time as a batch charge, and then the same 1,1,1,3,3-pentachloropropane or 1,1,1,3,3-pentachloropropane and/or 1,1,3,3-tetrachloropropene and/or 1,3,3,3-tetrachloropropene mixture can be added gradually to the reactor (a semi-batch operation). Proper temperature control of the coolant and sufficient reflux action are desirable for optimum operation of the stripping column to be effective. General operating conditions which we have found to work well for the reaction and stripping are: Operating pressure of 80-140 psig maintained by a control valve on the exiting flow from the stripper column; reactor temperature of 85-120° C., primarily supplied by steam flow into the reactor jacket; application of −40° C.-25° C. brine cooling to the heat exchanger on top of the stripper column to induce reflux; temperature in the center portion of the stripper about 10-40° C. below that in the reactor; additional heat input by superheating the HF vapor feed with high-pressure steam to 120-150° C.; feed rate of HF to maintain reactor and stripper conditions, typically 0.5 to 2.0 pounds per hour in apparatus of this size.

It has been discovered that maintaining the reaction under the operating conditions, particularly, a temperature range of 85-120° C., more preferably 90-110° C., and most preferably 95-100° C., produces an unexpected shift in the reaction mechanism which produces a high ratio of 1233zd(E) compared to 1233zd (Z).

Unit Operation Three: Removal of HCl

The HCl formed continuously during the reaction is removed from the reactor due to its volatile nature, and flows through the attached distillation column without condensing. The material can then be purified and collected for sale (or further purification) by using a low-temperature HCl distillation column. High purity HCl is isolated and can be absorbed in de-ionized water as concentrated HCl for sale.

Unit Operation Four: Separation and Recycle of Excess HF Back to Unit Operation Two The bottoms stream from the HCl removal column (unit operation three) contains a crude product mixture of 1233zd (E) and HF (in some embodiments about 30 wt %) is fed to a sulfuric extractor Or a phase separator for removal of HF from this mixture. HF is either dissolved in the sulfuric acid or phase separated from the organic mixture. For embodiments utilizing a sulfuric acid adsorption system, the HF is then desorbed from the sulfuric acid/HF mixture by stripping distillation and recycled back to the reactor. For embodiments utilizing a phase separator, HF is phase-separated and recycled back to the reactor. The organic mixture either from the overhead of the sulfuric acid extractor or from the bottom layer of the phase separator may require treatment (scrubbing or adsorption) to remove traces of HF before it is fed to the next unit operation.

Unit Operation Five: Purification of Final Product

Purification of final product preferably comprises two continuously operating distillation columns. The $1^{st}$ column is used to remove light ends from the 1233zd(E) and the $2^{nd}$ column is used to remove the heavier components, primarily the 1233zd(Z), which is fed to an isomerization reactor, collected for further use or optionally recycled back to the reactor (i.e., unit operation two). In certain embodiments, it is desirable to have a purge of heavy by-products from this stream.

Unit Operation Six: Isomerization of by-Product 1233zd (Z) to 1233zd(E)

To maximize the 1233zd(E) yield in this process, the by-product 1233zd (Z) formed in the reaction and exiting the bottom of the $2^{nd}$ column is fed as a vapor to a reactor that contains an isomerization catalyst, preferably fluorinated chromium oxide. Here, the by-product is converted to the desired product. The isomerization reactor exit stream is then recycled to unit operation four for purification.

In certain preferred embodiments, this step involves controlling the temperature of a heated surface to greater than 50° C.-350° C. The heated surface is contacted with the stream containing the 1233zd(Z) by-product. The feed stream is contacted with the heated surface for a period of time sufficient to convert at least a portion of the 1233zd(Z) to 1233zd (E) to produce a product stream rich in 1233zd(E).

In some embodiments, the heated surface includes the inside of a reactor vessel. In addition, or in the alternative, the heated surface may include an outer surface of a packing material, for example a packing material that is packed in a reaction vessel. In some embodiments, the reactor vessel is a batch-wise reactor vessel that can be charged with the feed stream. In some such embodiments, the feed stream may be sealed in the batch-wise reactor, and, after sufficient time passes to isomerize the desired amount of 1233zd(Z), the reactor vessel may be opened to remove the product stream. In other embodiments, the reactor vessel is a continuous-type reactor vessel, for example a reactor vessel with a first opening and a second opening and a fluid pathway between the first and second openings. The feed stream is fed into the reactor vessel through the first opening and passes through the reactor vessel at a rate sufficient to isomerize the desired amount of 1233zd(Z). The resulting product stream exits the second opening. In one example, the reactor vessel is an elongate reactor vessel (e.g., a MONEL™ tube) with the first opening at a first end and the second opening at a second end.

In some embodiments, the reactor vessel may be partially or entirely packed with packing material, for example with a stainless steel packing. In some embodiments, the relatively large surface area of the packing material may facilitate the conversion reaction from the (Z) to the (E) isomer. Support structures that support the packing material may also be disposed in or on the reactor vessel. For example, the packing material may be supported by a mesh or other structure that is disposed under, around, and/or within the packing material. The support structure may comprise the same material as the packing material (e.g., stainless steel), nickel, or any other suitable material.

The packing materials may also comprise one or more catalyst materials. Examples of suitable catalysts for the isomerization of 1233zd are metal oxides, halogenated metal oxides, Lewis acid metal halides, zero-valent metals, as well as combinations of these catalysts. Specific examples of suitable catalysts are $AlF_3$, $Cr_2O_3$, fluorinated. $Cr_2O_3$, zirconium oxide and halogenated versions thereof, or an aluminum oxide and halogenated versions thereof. In addition, the catalysts may be activated prior to use. Examples of activation procedures for several suitable catalysts may be found in U.S. Publication No. 2008-0103342, which is hereby incorporated by reference in its entirety.

Turning to the Figures, FIG. 1 shows the synthesis of 1233zd(E) via a liquid phase reaction integrated process having a sulfuric acid HF recovery system. Here, liquid phase reactor R1 is first charged with an amount of anhydrous hydrogen fluoride that is in a stoichiometric excess of the amount needed to totally fluorinate a metal chloride catalyst fluorination catalyst, e.g. when using $TiCl_4$ a>4:1 mole ratio of HF to catalyst is added. This is followed by the addition of a fluorination catalyst alone or in combination from the group comprising $TiCl_4$, $SnCl_4$, $TaCl_5$, $SbCl_3$, $FeCl_3$, or $AlCl_3$ to prepare the catalyst. $TiCl_4$ is most preferred. The catalyst preparation is done while the reactor is at 0-120° C. HCl is generated during catalyst preparation and can be vented out of the top of the catalyst stripper column CS-1 to control the reactor pressure at or below the intended operating pressure of the reactor. Preferably the reactor is constructed from materials which are resistant to the corrosive effects of the HF and catalyst, such as Hastelloy-C, Inconel, Monel, Incolloy, or fluoropolymer-lined steel vessels. Such liquid-phase fluorination reactors are well known in the art. Additional HF and 1,1,1,3,3-pentachloropropane or 1,1,1,3,3-pentachloropropane and/or 1,1,3,3-tetrachloropropene and/or 1,3,3,3-tetrachloropropene mixture is then added until good agitation is achieved.

The reaction mixture is then heated to about 85° C. where the fluorination reaction between HCC-240fa and HF is initiated. Continuous 1,1,1,3,3-pentachloropropane or 1,1,1,3,3-pentachloropropane and/or 1,1,3,3-tetrachloropropene and/or 1,3,3,3-tetrachloropropene mixture and HF (in a stoiciometric excess) feeds are simultaneously fed to heater HX-1 and then into a liquid phase reactor R-1. Optionally, 1,1,1,3,3-pentachloropropane or 1,1,1,3,3-pentachloropropane and/or 1,1,3,3-tetrachloropropene and/or 1,3,3,3-tetrachloropropene mixture is fed directly into reactor R-1 and not through heater HX-1. The operating pressure of 60-160 psig (preferably 80-140 psig) is maintained by a control valve on the exiting flow from the catalyst stripper column CS-1 and the reactor temperature is kept in the range of 85-120° C., primarily supplied by steam flow into the reactor jacket. A catalyst shipper column CS-1 is connected to the reactor, R-1, and serves the purpose of knocking down and returning entrained catalyst, some HF, partially fluorinated intermediates, and some unreacted 1,1,1,3,3-pentachloropropane, and/or 1,1,3,3-tetrachloropropene and/or 1,3,3,3-tetrachloropropene back to the reactor for further reaction.

The stream exiting the top of catalyst stripper CS-1 comprising mainly 1233zd(E), 1233zd(Z), HF, and HCl (with some minor components including partially fluorinated intermediates and by-products, overfluorinated by-products, and 1233zd dimers), then enters HCl column D-1. A stream comprising mainly HCl by-product exits the top of the HCl column and is fed to an HCl recovery system. The recovered HCl by-product can be sold for profit. The HCl column bottoms stream consisting mainly of 1233zd(E), 1233zd(Z), and HF are then fed into an HF recovery system. The HF recovery system starts with the crude 1233zd/HF stream being vaporized in heat exchanger HX-2 and fed into HF absorption column A-1. Here a liquid stream of 50-80% $H_2SO_4$ contacts the gaseous 1233zd/HF stream and absorbs the majority of the HF. The stream exiting the bottom of A-1 comprises $HF/H_2SO_4/H_2O$ and is fed to heat exchanger HX-3 where it is heated to a temperature sufficient to flash the majority of the HF along with small amounts of $H_2O$ and $H_2SO_4$. This stream is fed to HF recovery distillation column D-2. The liquid remaining after the HF is flashed off in HX-3 consisting mainly of $H_2SO_4$ and $H_2O$ (with 0-2% HF) is cooled in HX-4 and recycled back to HF absorption column A-1. The HF recovery column, D-2, bottoms stream comprising mainly $H_2SO_4$ and $H_2O$ are recycled back to heat exchanger HX-3. Anhydrous HF is recovered from the top of the HF recovery column, D-2, and is recycled back to the reactor R-1 via vaporizer HX-1. The stream exiting the top of HF absorption column A-1 comprising mainly 1233zd (E) and 1233zd(Z) (trace HF) is sent forward to a polishing system A-2 where the gaseous stream contacts a water or a caustic solution to remove trace HF and is subsequently dried with a desiccant. Acid free crude product exiting absorber A-2 is sent to the first of two purification columns, D-3. A stream exiting the top of the column D-3 consists mainly of reaction by-products that have boiling points lower than that of 1233zd(E). The stream exiting the bottom of lights column D-3 consisting mainly of 1233zd(E) and 1233zd(Z) and heavier by-products is fed to product recovery distillation column D-4. Product grade 1233zd(E) exits the top of the column to product storage. The product column bottoms consist mainly of 1233zd(Z) and reaction by-products with boiling points higher than that of HCFO-1233zd(E) is then fed to vaporizer HX-5 and then to isomerization reactor R-2 where by-product 1233zd (Z) is converted to the desired product. The stream leaving R-2 is then recycled to lights distillation column D-3 for purification. Optionally, if any by-products in the stream entering R-2 are unstable they may decompose and form small amounts of HF or HCl. In this case, the stream exiting R-2 can be recycled and combined with the stream entering the polishing system A-2 to remove the acid. Optionally, the stream exiting the bottom of the product recovery distillation column, D-4 can be recycled back to liquid phase reactor R-1. In any of these options a heavies purge stream from the bottom of the product recovery distillation column, D-4, will be required to prevent build-up of high boiling impurities in the purification system. The heavies purge stream is collected for later use or waste disposal.

Figure 2:
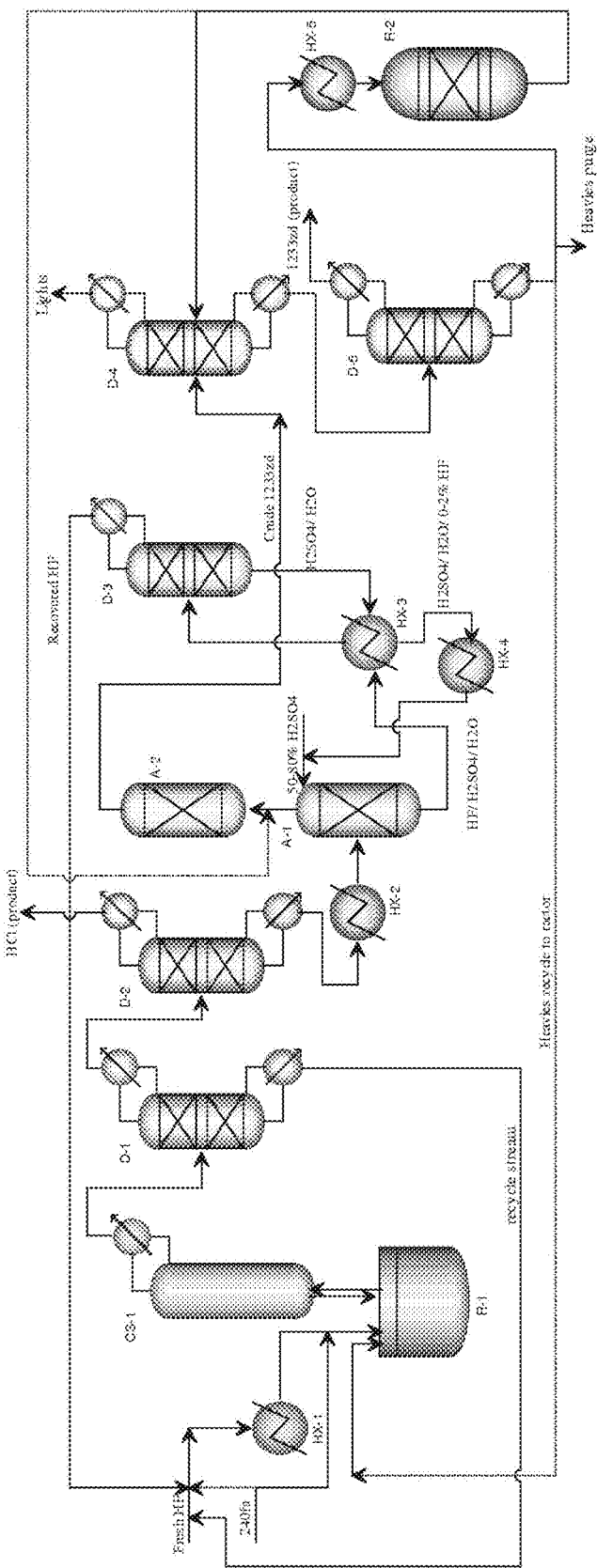
FIG. 2 shows a schematic depiction of an integrated liquid phase synthesis of 1233zd(E) according to another preferred embodiment of the invention.

Referring to FIG. 2, shown is the synthesis of 1233zd(E) via a liquid phase reaction integrated process having sulfuric acid HF recovery and optional recycle column after the reactor. Here, liquid phase reactor R1 is first charged with an amount of anhydrous hydrogen fluoride that is in a stoichiometric excess of the amount needed to totally fluorinate a metal chloride catalyst fluorination catalyst, e.g. when using $TiCl_4$ a>4:1 mole ratio of HF to catalyst is added. This is followed by the addition of a fluorination catalyst alone or in combination from the group comprising $TiCl_4$, $SnCl_4$, $TaCl_5$, $SbCl_3$, $FeCl_3$, or $AlCl_3$ to prepare the catalyst. $TiCl_4$ is most preferred. The catalyst preparation is done while the reactor is at 0-120° C. HCl is generated during catalyst preparation and can be vented out of the top of the catalyst stripper column CS-1 to control the reactor pressure at or below the intended operating pressure of the reactor. Preferably the reactor is constructed from materials which are resistant to the corrosive effects of the HF and catalyst, such as Hastelloy-C, Inconel, Monel, Incolloy, or fruoropolymer-lined steel vessels. Such liquid-phase fluorination reactors are well known in the art. Additional HF and 1,1,1,3,3-pentachloropropane or 1,1,1,3,3-pentachloropropane and/or 1,1,3,3-tetrachloropropene and/or 1,3,3,3-tetrachloropropene mixture is then added until good agitation is achieved.

The reaction mixture is then heated to about 85° C. where the fluorination reaction between 1,1,1,3,3-pentachloropropane or 1,1,1,3,3-pentachloropropane and/or 1,1,3,3-tetrachloropropene and/or 1,3,3,3-tetrachloropropene mixture and HF is initiated. Continuous 1,1,1,3,3-pentachloropropane or 1,1,1,3,3-pentachloropropane and/or 1,1,3,3-tetrachloropropene and/or 1,3,3,3-tetrachloropropene mixture and HF (in a stoiciometric excess) feeds are simultaneously fed to heater HX-1 and then into a liquid phase reactor R-1. Optionally, 1,1,1,3,3-pentachloropropane or 1,1,1,3,3-pentachloropropane and/or 1,1,3,3-tetrachloropropene and/or 1,3,3,3-tetrachloropropene mixture is fed directly into reactor R-1 and not through heater HX-1. The operating pressure of 60-160 psig (preferably 80-140 psig) is maintained by a control valve on the exiting flow from the catalyst stripper column CS-1 and the reactor temperature is kept in the range of 85-120° C. primarily supplied by steam flow into the reactor jacket. A catalyst stripper column CS-1 is connected to the reactor, R-1, and serves the purpose of knocking down and returning entrained catalyst, some HF, partially fluorinated intermediates, and some unreacted 1,1,1,3,3-pentachloropropane, 1,1,3,3-tetrachloropropene or 1,3,3,3-tetrachloropropene back to the reactor for further reaction.

The stream exiting the top of catalyst stripper CS-1 comprising mainly 1233zd(E), 1233zd(Z), HF, and HCl (with some minor components including partially fluorinated intermediates and by-products, overfluorinated by-products, and 1233zd dimers), then enters then enters recycle column D-1 where a stream comprising mainly unreacted 1,1,1,3,3-pentachloropropane, and/or 1,1,3,3-tetrachloropropene and/or 1,3,3,3-tetrachloropropene, partially fluorinated intermediates, 1233zd dimers, and the majority of the HF exits the bottom of the recycle column and is recycled back to the liquid phase reactor R-1 via vaporizer HX-1. A stream comprising mainly 1233zd(E), 1233zd(Z), HF, and HCl exits the top of the recycle column and enters HCl column D-2. A stream comprising mainly HCl by-product exits the top of the HCl column and is fed to an HCl recovery system. The recovered HCl by-product can be sold for profit. The HCl column bottoms stream consisting mainly of 1233zd(E), 1233zd(Z), and HF are then fed into an HF recovery system. The HF recovery system starts with the crude 1233zd/HF stream being vaporized in heat exchanger HX-2 and fed into HF absorption column A-1. Here a liquid stream of 50-80% $H_2SO_4$ contacts the gaseous 1233zd/HF stream and absorbs the majority of the HF. The stream exiting the bottom of A-1 comprises $HF/H_2SO_4/H_2O$ and is fed to heat exchanger HX-3 where it is heated to a temperature sufficient to flash the majority of the HF along with small amounts of $H_2O$ and $H_2SO_4$. This stream is fed to HF recovery distillation column D-2. The liquid remaining after the HF is flashed off in HX-3 consisting mainly of $H_2SO_4$ and $H_2O$ (with 0-2% HF) is cooled in HX-4 and recycled back to HF absorption column A-1. The HF recovery column, D-3, bottoms stream comprising mainly $H_2SO_4$ and $H_2O$ are recycled back to heat exchanger HX-3. Anhydrous HF is recovered from the top of the HF recovery column, D-3, and is recycled back to the reactor R-1 via vaporizer HX-1. The stream exiting the top of HF absorption column A-1 comprising mainly 1233zd(E) and 1233zd(Z) (trace HF) is sent forward to a polishing system A-2 where the gaseous stream contacts a water or a caustic solution to remove trace HF and is subsequently dried with a desiccant. Acid free crude product exiting absorber A-2 is sent to the first of two purification columns, D-4. A stream exiting the top of the column D-4 consists mainly of reaction by-products that have boiling points lower than that of 1233zd (E). The stream exiting the bottom of lights column D-4 consisting mainly of 1233zd(E) and 1233zd(Z) and heavier by-products is fed to product recovery distillation column D-5. Product grade 1233zd(E) exits the top of the column to product storage. The product column bottoms consist mainly of 1233zd(Z) and reaction by-products with boiling points higher than that of 1233zd(E) is then fed to vaporizer HX-5 and then to isomerization reactor R-2 where by-product 1233zd (Z) is converted to the desired product. The stream leaving R-2 is then recycled to lights distillation column D-4 for purification. Optionally, if any by-products in the stream entering R-2 are unstable they may decompose and form small amounts of HF or HCl. In this case the stream exiting R-2 can be recycled and combined with the stream entering the polishing system A-2 to remove the acid. Optionally, the stream exiting the bottom of the product recovery distillation column, D-5 can be recycled back to liquid phase reactor R-1. In any of these options a heavies purge stream from the bottom of the product recovery distillation column, D-5, will be required to prevent build-up of high boiling impurities in the purification system. The heavies purge stream is collected for later use or waste disposal.

Figure 3:
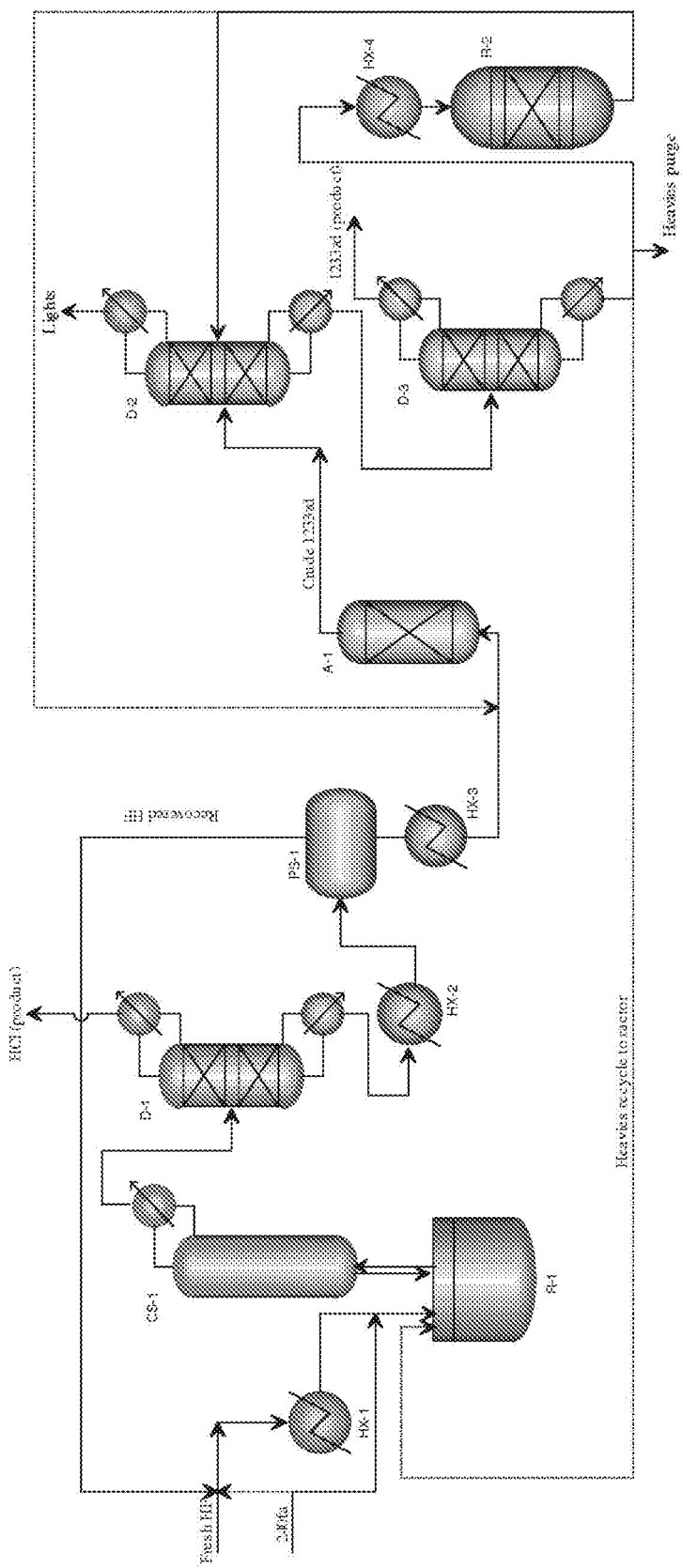
FIG. 3 shows a schematic depiction of an integrated liquid phase synthesis of 1233zd(E) according to another preferred embodiment of the invention.

Referring to FIG. 3, shown is the synthesis of 1233zd(E) via a liquid phase reaction integrated process having a phase separation HF recovery system. Here, liquid phase reactor R1 is first charged with an amount of anhydrous hydrogen fluoride that is in a stoichiometric excess of the amount needed to totally fluorinate a metal chloride catalyst fluorination catalyst. E.g. when using $TiCl_4$ a>4:1 mole ratio of HF to catalyst is added. This is followed by the addition of a fluorination catalyst alone or in combination from the group comprising $TiCl_4$, $SnCl_4$, $TaCl_5$, $SbCl_3$, $FeCl_3$, or $AlCl_3$ to prepare the catalyst. $TiCl_4$ is most preferred. The catalyst preparation is done while the reactor is at 0-120° C.

HCl is generated during catalyst preparation and can be vented out of the top of the catalyst stripper column CS-1 to control the reactor pressure at or below the intended operating pressure of the reactor. Preferably the reactor is constructed from materials which are resistant to the corrosive effects of the HF and catalyst, such as Hastelloy-C, Inconel, Monel, Incolloy, or fluoropolymer-lined steel vessels. Such liquid-phase fluorination reactors are well known in the art. Additional HF and 1,1,1,3,3-pentachloropropane or 1,1,1,3,3-pentachloropropane and/or 1,1,3,3-tetrachloropropene and/or 1,3,3,3-tetrachloropropene mixture is then added until good agitation is achieved.

The reaction mixture is then heated to about 85° C. where the fluorination reaction between 1,1,1,3,3-pentachloropropane or 1,1,1,3,3-pentachloropropane and/or 1,1,3,3-tetrachloropropene and/or 1,3,3,3-tetrachloropropene mixture and HF is initiated. Continuous 1,1,1,3,3-pentachloropropane or 1,1,1,3,3-pentachloropropane and/or 1,1,3,3-tetrachloropropene and/or 1,3,3,3-tetrachloropropene mixture and HF (in a stoiciometric excess) feeds are simultaneously fed to heater HX-1 and then into a liquid phase reactor R-1. Optionally, 1,1,1,3,3-pentachloropropane or 1,1,1,3,3-pentachloropropane and/or 1,1,3,3-tetrachloropropene and/or 1,3,3,3-tetrachloropropene mixture is fed directly into reactor R-1 and not through heater HX-1. The operating pressure of 60-160 psig (preferably 80-140 psig) is maintained by a control valve on the exiting flow from the catalyst stripper column CS-1 and the reactor temperature is kept in the range of 85-120° C. primarily supplied by steam flow into the reactor jacket. A catalyst stripper column CS-1 is connected to the reactor, R-1, and serves the purpose of knocking down and returning entrained catalyst, some HF, partially fluorinated intermediates, and some unreacted 1,1,1,3,3-pentachloropropane and/or 1,1,3,3-tetrachloropropene and/or 1,3,3,3-tetrachloropropene back to the reactor for further reaction.

The stream exiting the top of catalyst stripper CS-1 comprising mainly 1233zd(E), 1233zd(Z), HF, and HCl (with some minor components including partially fluorinated intermediates and by-products, overfluorinated by-products, and 1233zd dimers), then enters HCl column D-1. A stream comprising mainly HCl by-product exits the top of the HCl column and is fed to an HCl recovery system. The recovered HCl by-product can be sold for profit. The HCl column bottoms stream consisting mainly of 1233zd(E), 1233zd(Z), and HF are then fed into an HF recovery system. The HF recovery system starts with the 1233zd/HF stream being fed into heat exchanger HX-2 where it is pre-cooled to temperatures <0° C. and then enters phase separation vessel PS-1. Here the stream temperature is maintained or further cooled to −40-−5° C. The HF rich top layer (<10% 1233zd) is recycled back to the liquid phase reactor R-1. The organic rich bottom layer containing mainly 1233zd (<4% HF) is sent to vaporizer HX-3 and then forward to a polishing system A-1 where the gaseous stream contacts a water or a caustic solution to remove trace HF and is subsequently dried with a desiccant. Acid free crude product exiting absorber A-1 is sent to the first of two purification columns, D-2. A stream exiting the top of the column D-2 consists mainly of reaction by-products that have boiling points lower than that of 1233zd(E). The stream exiting the bottom of lights column D-2 consisting mainly of 1233zd(E) and 1233zd(Z) and heavier by-products is fed to product recovery distillation column D-3. Product grade 1233zd(E) exits the top of the column to product storage. The product column bottoms consist mainly of 1233zd(Z) and reaction by-products with boiling points higher than that of 1233zd (E) is then fed to vaporizer HX-4 and then to isomerization reactor R-2 where by-product 133zd (Z) is converted to the desired product. The stream leaving R-2 is then recycled to lights distillation column D-2 for purification. Optionally, if any by-products in the stream entering R-2 are unstable they may decompose and form small amounts of HF or HCl. In this case the stream exiting R-2 can be recycled and combined with the stream entering the polishing system A-1 to remove the acid. Optionally, the stream exiting the bottom of the product recovery distillation column, D-3 can be recycled back to liquid phase reactor R-1. In any of these options a heavies purge stream from the bottom of the product recovery distillation column, D-3, will be required to prevent build-up of high boiling impurities in the purification system. The heavies purge stream is collected for later use or waste disposal.

Figure 4:
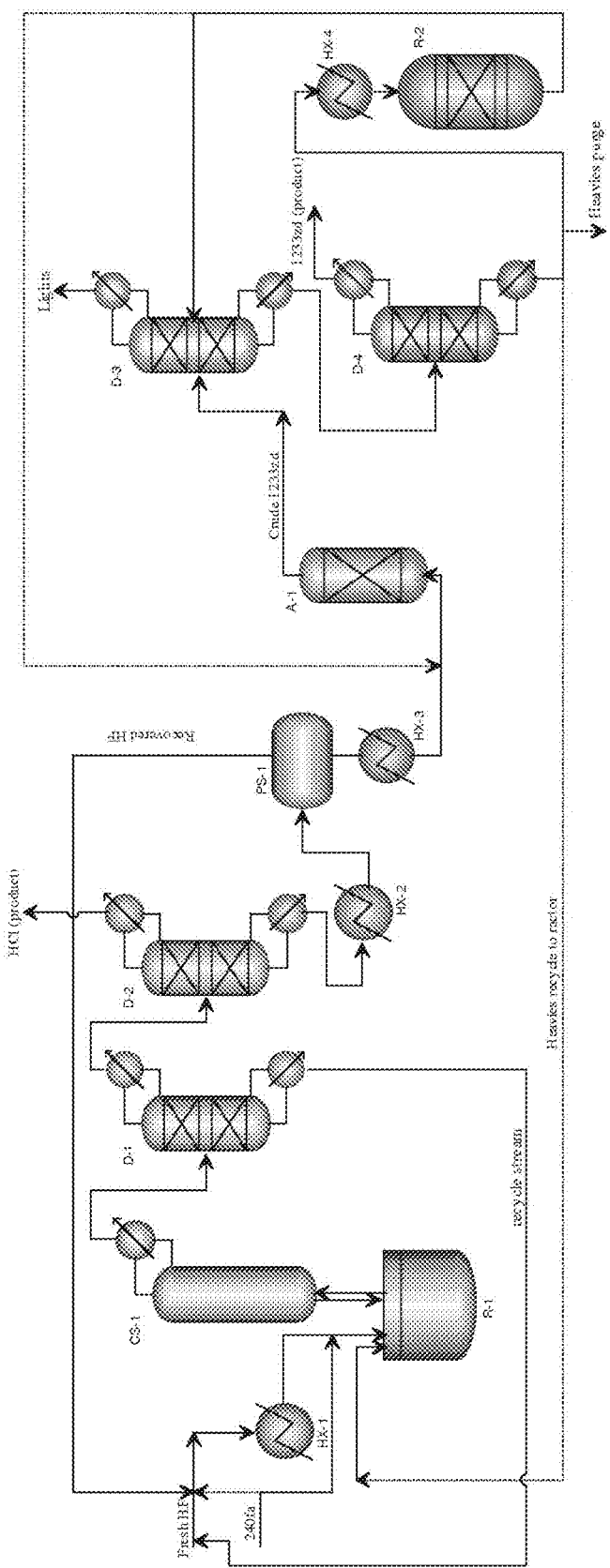
FIG. 4 shows a schematic depiction of an integrated liquid phase synthesis of 1233zd(E) according to yet another preferred embodiment of the invention.

Referring to FIG. 4, shown is the synthesis of 1233zd(E) via a liquid phase reaction integrated process having a phase separation HF recovery system and optional recycle column after reactor. Liquid phase reactor R1 is first charged with an amount of anhydrous hydrogen fluoride that is in a stoichiometric excess of the amount needed to totally fluorinate a metal chloride catalyst fluorination catalyst. E.g. when using $TiCl_4$ a>4:1 mole ratio of HF to catalyst is added. This is followed by the addition of a fluorination catalyst alone or in combination from the group comprising $TiCl_4$, $SnCl_4$, $TaCl_5$, $SbCl_3$, $FeCl_3$, or $AlCl_3$ to prepare the catalyst. $TiCl_4$ is most preferred. The catalyst preparation is done while the reactor is at 0-120° C. HCl is generated during catalyst preparation and can be vented out of the top of the catalyst stripper column CS-1 to control the reactor pressure at or below the intended operating pressure of the reactor. Preferably the reactor is constructed from materials which are resistant to the corrosive effects of the HF and catalyst, such as Hastelloy-C, Inconel, Monel, Incolloy, or fluoropolymer-lined steel vessels. Such liquid-phase fluorination reactors are well known in the art. Additional HF and 1,1,1,3,3-pentachloropropane or 1,1,1,3,3-pentachloropropane and/or 1,1,3,3-tetrachloropropene and/or 1,3,3,3-tetrachloropropene mixture is then added until good agitation is achieved.

The reaction mixture is then heated to about 85° C. where the fluorination reaction between 1,1,1,3,3-pentachloropropane or 1,1,1,3,3-pentachloropropane and/or 1,1,3,3-tetrachloropropene and/or 1,3,3,3-tetrachloropropene mixture and HF is initiated. Continuous 1,1,1,3,3-pentachloropropane or 1,1,1,3,3-pentachloropropane and/or 1,1,3,3-tetrachloropropene and/or 1,3,3,3-tetrachloropropene mixture and HF (in a stoiciometric excess) feeds are simultaneously fed to heater HX-1 and then into a liquid phase reactor R-1. Optionally, 1,1,1,3,3-pentachloropropane or 1,1,1,3,3-pentachloropropane and/or 1,1,3,3-tetrachloropropene and/or 1,3,3,3-tetrachloropropene mixture is fed directly into reactor R-1 and not through heater HX-1. The operating pressure of 60-160 psig (preferably 80-140 psig) is maintained by a control valve on the exiting flow from the catalyst stripper column CS-1 and the reactor temperature is kept in the range of 85-120° C. primarily supplied by steam flow into the reactor jacket. A catalyst stripper column CS-1 is connected to the reactor, R-1, and serves the purpose of knocking down and returning entrained catalyst, some HF, partially fluorinated intermediates, and some unreacted 1,1,1,3,3-pentachloropropane and/or 1,1,3,3-tetrachloropropene and/or 1,3,3,3-tetrachloropropene back to the reactor for further reaction.

The stream exiting the top of catalyst stripper CS-1 comprising mainly 1233zd(E), 1233zd(Z), HF, and HCl (with some minor components including partially fluorinated intermediates and by-products, overfluorinated by-products, and 1233zd dimers), then enters then enters recycle column D-1 where a stream comprising mainly unreacted 1,1,1,3,3-pentachloropropane and/or 1,1,3,3-tetrachloropropene and/or 1,3,3,3-tetrachloropropene, partially fluorinated intermediates, 1233zd dimers, and the majority of the HF exits the bottom of the recycle column and is recycled back to the liquid phase reactor R-1 via vaporizer HX-1. A stream comprising mainly 1233zd(E), 1233zd(Z), HF, and HCl exits the top of the recycle column and enters HCl column D-2. A stream comprising mainly HCl by-product exits the top of the HCl column and is fed to an HCl recovery system. The recovered HCl by-product can be sold for profit. The HCl column bottoms stream consisting mainly of 1233zd(E), 1233zd(Z), and HF are then fed into an HF recovery system. The HF recovery system starts with the 1233zd/HF stream being fed into heat exchanger HX-2 where it is pre-cooled to temperatures <0° C. and then enters phase separation vessel PS-1. Here the stream temperature is maintained or further cooled to −40-0° C. The HF rich top layer (<10% 1233zd) is recycled back to the liquid phase reactor R-1. The organic rich bottom layer containing mainly 1233zd (<4% HF) is sent to vaporizer HX-3 and then forward to a polishing system A-1 where the gaseous stream contacts a water or a caustic solution to remove trace HF and is subsequently dried with a desiccant. Acid free crude product exiting absorber A-1 is sent to the first of two purification columns, D-3. A stream exiting the top of the column D-3 consists mainly of reaction by-products that have boiling points lower than that of 1233zd(E). The stream exiting the bottom of lights column D-3 consisting mainly of 1233zd(E) and 1233zd(Z) and heavier by-products is fed to product recovery distillation column D-4. Product grade 1233zd(E) exits the top of the column to product storage. The product column bottoms consist mainly of 1233zd(Z) and reaction by-products with boiling points higher than that of 1233zd(E) is then fed to vaporizer HX-4 and then to isomerization reactor R-2 where by-product 1233zd (Z) is converted to the desired product. The stream leaving R-2 is then recycled to lights distillation column D-3 for purification. Optionally, if any by-products in the stream entering R-2 are unstable they may decompose and form small amounts of HF or HCl. In this case the stream exiting R-2 can be recycled and combined with the stream entering the polishing system A-1 to remove the acid. Optionally, the stream exiting the bottom of the product recovery distillation column, D-4 can be recycled back to liquid phase reactor R-1. In any of these options a heavies purge stream from the bottom of the product recovery distillation column, D-4, will be required to prevent build-up of high boiling impurities in the purification system. The heavies purge stream is collected for later use or waste disposal.

Vapor Phase Reaction

The reaction chemistry for the vapor phase process involves a single-step reaction of 1,1,1,3,3-pentachloropropane (HCC-240fa) with anhydrous HF in a vapor phase reactor to produce a mixture of HCFO-1233zd (1-chloro-3,3,3-trifluoropropene) and HCl. Preferably, though not exclusively, the reaction is maintained under conditions (e.g. temperature, pressure, residence time, etc.) to increase the relative ratio of (E) to (Z) isomers of HCFO-1233zd. The instant reaction also minimizes the undesirable reaction of HF with the resulting HCFO-1233zd(E), which produces HCF-244fa and/or HCF-245fa, either of which proceeds to the formation of HFO-1234ze (as illustrated below).

Accordingly, in one embodiment, the desired reaction of the instant invention is illustrated as follows:

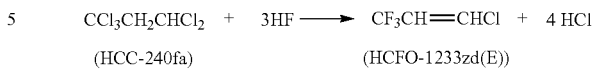

In a second embodiment, the undesired reactions of the instant invention are illustrated as follows:

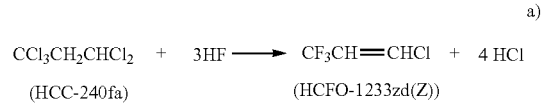

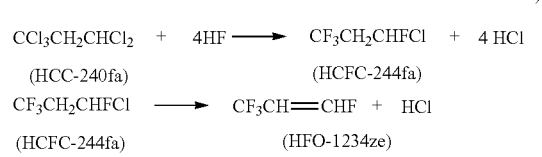

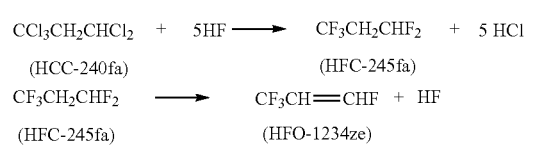

In certain embodiments, the manufacturing process comprises five major unit operations: (1) continuous mode fluorination reaction using HF, (2) separation and purification of at least byproduct HCl, (3) separation of excess HF back to (1), (4) production/purification of final product, HCFO-1233zd(E) with optional recycle of high-boilers back to (I), and (5) isomerization of by-product HCFO-1233zd(Z) to 1233zd (E). This maximizes process yield. The relative positions of these operations are shown in FIGS. 5-8, and are discussed in greater detail below.

Unit Operation One: Catalytic fluorination of 1,1,1,3,3-pentachloropropane

The fluorination reaction described herein uses a vapor phase catalyst of sufficient strength and reaction conditions to achieve the desired reaction product, i.e. HCFO-1233zd (E)

The fluorination catalyst may include any vapor phase fluorination catalyst that is known in the art. Suitable catalysts include, but are not limited to, chromium, aluminum, cobalt, manganese, nickel and iron oxides, hydroxides, halides, oxyhalides, inorganic salts thereof and their mixtures, which may be supported or in bulk. The vapor phase fluorination catalyst may also include combinations of known catalysts, such as, but not limited to, $Cr_2O_3$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Additional fluorination catalysts that can be used include, but are also not limited to, $FeCl_3/C$, $SnCl_4/C$, $TaCl_5/C$, $SbCl_3/C$; $AlCl_3/C$, and $AlF_3/C$. Supports for the metal halides listed can also be alumina or fluorinated alumina. Any of the foregoing catalysts, as well as other catalysts not listed, may be partially or totally fluorinated by anhydrous HF.

In certain embodiments, the fluorination catalyst may include chromium (III) oxides, such as crystalline chromium oxide or amorphous chromium oxide. While not limited thereto, amorphous chromium oxide ($Cr_2O_3$) is most preferred vapor phase catalyst. It is a commercially available material in a variety of particle sizes and may be selected to enhance their effectiveness. In certain embodiments, it is provided having a purity of at least 98%. The fluorination catalyst is provided in any amount sufficient to drive the reaction, but also may be presented in excess.

This reaction may be conducted in a vapor phase reactor known in the art. Preferably, though not exclusively, the reactor is constructed from materials that are resistant to the corrosive effects of the HF and catalyst, such as Hastelloy-C, Inconel, Monel, Incalloy, or fluoropolymer-lined steel vessels. Such vapor-phase fluorination reactors are well known in the art.

Proper temperature and pressure control of the reaction are desirable for optimum conversion. In certain non-limiting embodiments, the reaction temperature should be about 200 to about 450° C. and the reaction pressure should be about 0 to about 160 psig pressure. In further embodiments, the reaction temperature should be between about 250 and 400° C. and the reaction pressure should be about 0 to about 140 psig pressure. In even further embodiments, the reaction temperature should be between about 275 and 375° C. and the reaction pressure should be about 2 to about 130 psig pressure. It has been surprisingly discovered that maintaining the reaction under these operating conditions, produces an unexpected shift in the reaction mechanism which produces a high ratio of HCFO-1233zd(E) compared to HCFO-1233zd(Z).

Unit Operation Two: Removal of HCl

The HCl containing reaction products stream continuously exits the reactor and flows into an attached HCl distillation column. The HCl material exits the top of the column and can then be further purified. High purity HCl can be isolated and absorbed in de-ionized water as concentrated HCl for other uses.

Unit Operation Three: Separation and Recycle of Excess HF

The bottom stream from the HCl removal column that contains crude product mixture of HCFO-1233zd(E) and HF (in some embodiments about 30 wt % to about 60 wt %) is fed to a sulfuric acid extractor or phase separator for removal of HF from this mixture. HF is either dissolved in the sulfuric acid or phase separated from the organic mixture. For embodiments utilizing a sulfuric acid adsorption system, the HF may be desorbed from the sulfuric acid/HF mixture by stripping distillation and recycled back to the reactor. For embodiments utilizing a phase separator, HF is phase-separated and recycled back to the reactor. The organic mixture either from the overhead of the sulfuric acid extractor or from the bottom layer of the phase separator may employ treatment (e.g. scrubbing or adsorption) to remove traces of HF before it is fed to the next unit operation (purification of the final product).

Unit Operation Four: Purification of the Final Product

Purification of the final product may include the use of one or more distillation columns. In certain embodiments, purification includes two or more continuously operating distillation columns. The first column is used to remove the lighter components from the mixture, such as HFO-1234ze. The second column may be used to removed heavier components, e.g. HCFO-1233zd(Z) and purify the final product, HCFO-1233zd(E). Such heavier components, if desirable, may be fed to an isomerization reactor, collected for further use, or optionally recycled back to the reactor. In certain embodiments, it is desirable to have a purge of heavy by-products from this stream.

Unit Operation Five: Isomerization of by-Product HCFO-1233Zd(Z) to HCFO-1233zd(E)

To maximize the HCFO-1233zd(E) yield in this process, the by-product HCFO-1233zd(Z) formed in the reaction and exiting the second column is fed as a vapor to a reactor that contains isomerization catalyst. The by-product is then converted to the desired product. The isomerization reactor exit stream is then recycled for purification, using the foregoing method. The isomerization reactor can be either the fluorination reactor discussed above or a separate isomerization reactor.

Catalysts may include, but are not limited to, any of the vapor phase catalysts discussed herein. In certain non-limiting embodiments, the catalyst is a fluorinated chromium oxide.

In certain preferred embodiments, this step involves controlling the temperature of a heated surface to greater than 50° C.-375° C. The heated surface is contacted with the stream containing the HCFO-1233zd(Z) by-product. The feed stream is contacted with the heated surface for a period of time sufficient to convert at least a portion of the 1233zd (Z) to 1233zd (E) to produce a product stream rich in 1233zd(E).

In some embodiments, the heated surface includes the inside of a reactor vessel. In addition, or in the alternative, the heated surface may include an outer surface of a packing material, for example a packing material that is packed in a reaction vessel. In some embodiments, the reactor vessel is a batch-wise reactor vessel that can be charged with the feed stream. In some such embodiments, the feed stream may be sealed in the batch-wise reactor, and, after sufficient time passes to isomerize the desired amount of HCFO-1233zd (Z), the reactor vessel may be opened to remove the product stream. In other embodiments, the reactor vessel is a continuous-type reactor vessel, for example a reactor vessel with a first opening and a second opening and a fluid pathway between the first and second openings. The feed stream is fed into the reactor vessel through the first opening and passes through the reactor vessel at a rate sufficient to isomerize the desired amount of HCFO-1233zd(Z). The resulting product stream exits the second opening. In one example, the reactor vessel is an elongate reactor vessel (e.g., a MONEL™ tube) with the first opening at a first end and the second opening at a second end.

In some embodiments, the reactorvessel may be partially or entirely packed with packing material, for example with a stainless steel packing. In some embodiments, the relatively large surface area of the packing material may facilitate the conversion reaction from the (Z) to the (E) isomer. Support structures that support the packing material may also be disposed in or on the reactor vessel. For example, the packing material may be supported by a mesh or other structure that is disposed under, around, and/or within the packing material. The support structure may comprise the same material as the packing material (e.g., stainless steel), nickel, or any other suitable material.

The packing materials may also comprise one or more catalyst materials. Examples of suitable catalysts for the isomerization of HCFO-1233zd are metal oxides, halogenated metal oxides, Lewis acid metal halides, zero-valent metals, as well as combinations of these catalysts. Specific examples of suitable catalysts are $AlF_3$, $Cr_2O_3$, fluorinated $Cr_2O_3$, zirconium oxide and halogenated versions thereof, or an aluminum oxide and halogenated versions thereof. In addition, the catalysts may be activated prior to use. Examples of activation procedures for several suitable catalysts may be found in U.S. Publication No. 2008-0103342, which is hereby incorporated by reference in its entirety.

Figure 5:
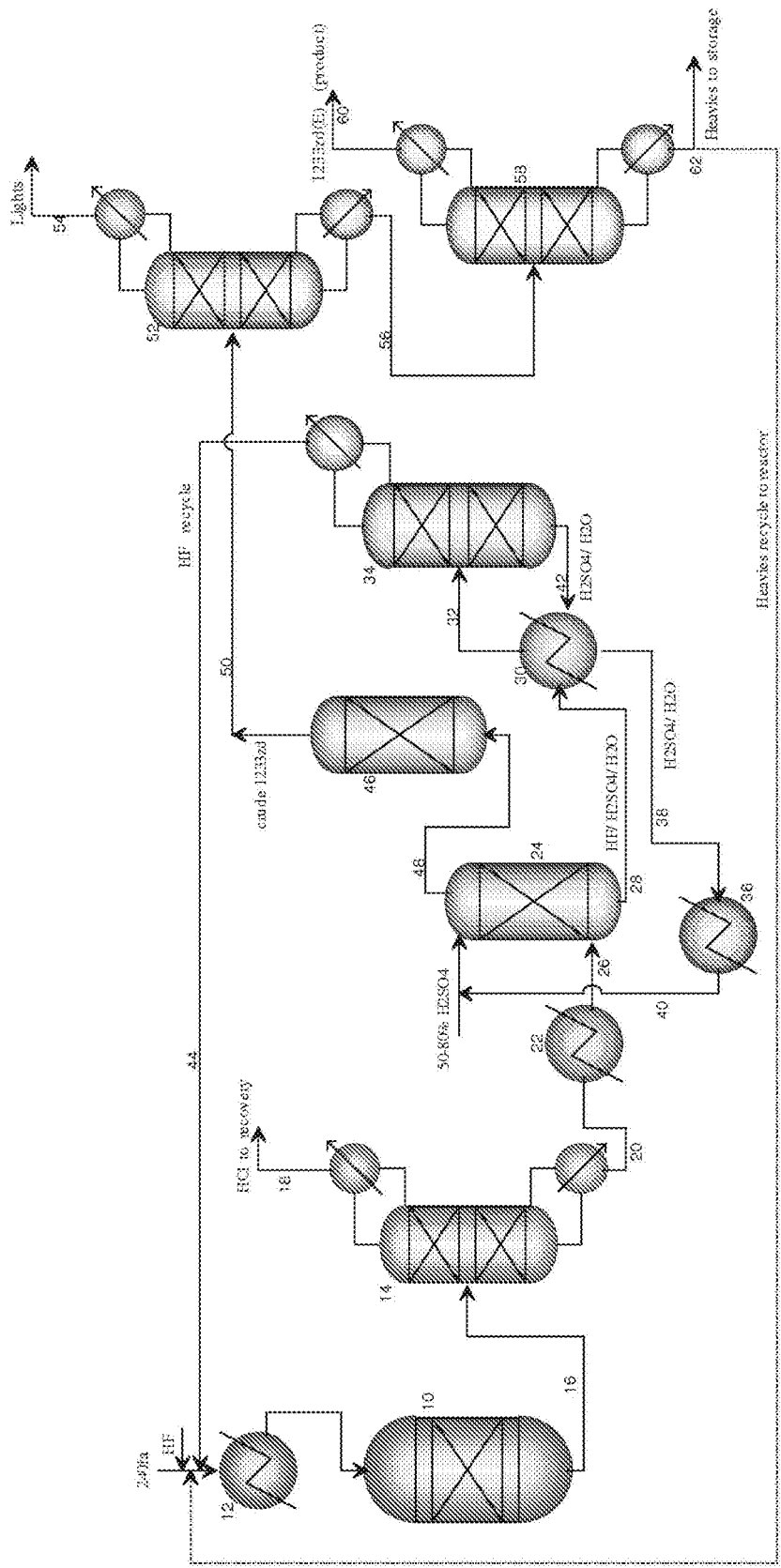
FIG. 5 is a schematic diagram of an example of a vapor phase system that produces (E)1-chloro-3,3,3-trifluoropropene.

Referring to FIG. 5 the synthesis of HCFO-1233zd(E) via a vapor phase reaction integrated process having a sulfuric acid HF recovery is illustrated. The vapor phase reactor 10 is first loaded with a fluorination catalyst, as discussed above. Catalysts can be supported or in bulk, with preferred, though non-limiting catalysts, being fluorinated chromium oxide.

HCC-240fa and HF are simultaneously fed to a vaporizer 12 and then into the vapor phase reactor 10. The reaction temperature may be about 200 to about 450° C. and at about 0 to about 160 psig pressure. The mole ratio of HF to HCC-240fa may be ≥3:1, preferably between 3:1 and 20:1, more preferably between 4:1 and 12:1, and most preferably between 5:1 and 11:1.

Reactor effluent including partially fluorinated intermediates and by-products, overfluorinated by-products, HF, HCFO-1233zd(E+Z) and HCl, then enters HCl column 14 through line 16. A stream of mainly HCl by-product exits the top portion of the HCl column 14 and is fed to an HCl recovery system through line 18. The recovered HCl by-product can be used for other purposes, as discussed herein.

The HCl column bottoms consisting mainly of partially fluorinated intermediates and by-products, overfluorinated by-products, HF and HCFO-1233zd(E+Z) are then fed via line 20 into an HF recovery system. The HF recovery system starts with the HCFO-1233zd/HF stream being vaporized in heat exchanger 22 and is then fed into HF absorption column 24 via line 26. Here, a liquid stream of 50-80% $H_2SO_4$ contacts the gaseous HCFO-1233zd/HF stream and absorbs the majority of the HF. The stream 28 exiting the bottom of column 24 includes HF, $H_2SO_4$ and $H_2O$ and is fed to heat exchanger 30 where it is heated to a temperature sufficient to flash the majority of the HF along with small amounts of $H_2O$ and $H_2SO_4$. This stream is fed via line 32 to HF recovery distillation column 34. The liquid remaining after the HF is flashed off in heat exchanger 30 including mainly $H_2SO_4$ and $H_2O$ (with 0-2% HF) is cooled in heat exchanger 36 via line 38 and recycled via line 40 back to HF absorption column 24. The HF recovery column 34 bottoms stream including mainly $H_2SO_4$ and $H_2O$ is recycled via line 42 back to heat exchanger 30.

Anhydrous HF is recovered from the top of the HF recovery column 34 and is recycled back to the reactor 10 via line 44 to vaporizer 12.

The stream exiting the top portion of HF absorption column 24 including mainly HCFO-1233zd (E+Z) (trace HF) is sent forward via line 48 to a polishing system 46 where the gaseous stream contacts water or a caustic solution to remove trace HF and is subsequently dried with a desiccant. Acid free crude product exiting absorber 46 is sent via line 50 to the first of two purification columns 52. A stream 54 exiting the top portion of the column 52 includes mainly of reaction by-products that have boiling points lower than that of HCFO-1233zd(E). The stream 56 exiting the bottom portion of lights column 52 consisting mainly of HCFO-1233zd(E+Z) and heavier by-products is fed to product recovery distillation column 58. Product grade HCFO-1233zd(E) exits the top portion of the column to product storage via line 60. The product column bottoms 62 includes mainly HCFO-1233zd(Z).

Reaction by-products with boiling points higher than that of HCFO-1233zd(E) are then fed to a vaporizer (not illustrated) and then to isomerization reactor (not illustrated) where by-product HCFO-1233zd(Z) is converted to the desired product. The stream leaving is then recycled to lights distillation column 52 for purification. Optionally, if any by-products in the stream entering are unstable, they may decompose and form small amounts of HF or HCl. In this case, the stream exiting can be recycled and combined with the stream entering the polishing system to remove the acid. Optionally, the stream exiting the bottom of the product recovery distillation column 58 can be recycled back to vapor phase reactor 10, where isomerization of Z to E isomer of HCFO-1233zd takes place. In any of these possibilities, a heavies purge stream from the bottom of the product recovery distillation column 58 prevents build-up of high boiling impurities in the purification system. The heavies purge stream is collected for later use or waste disposal. After deactivation of the catalyst in reactor 10 it can be regenerated in situ by heating to 300-400° C. and passing an oxidizing agent such as $O_2$ or $Cl_2$ over the catalyst for a selected period of time.

Figure 6:
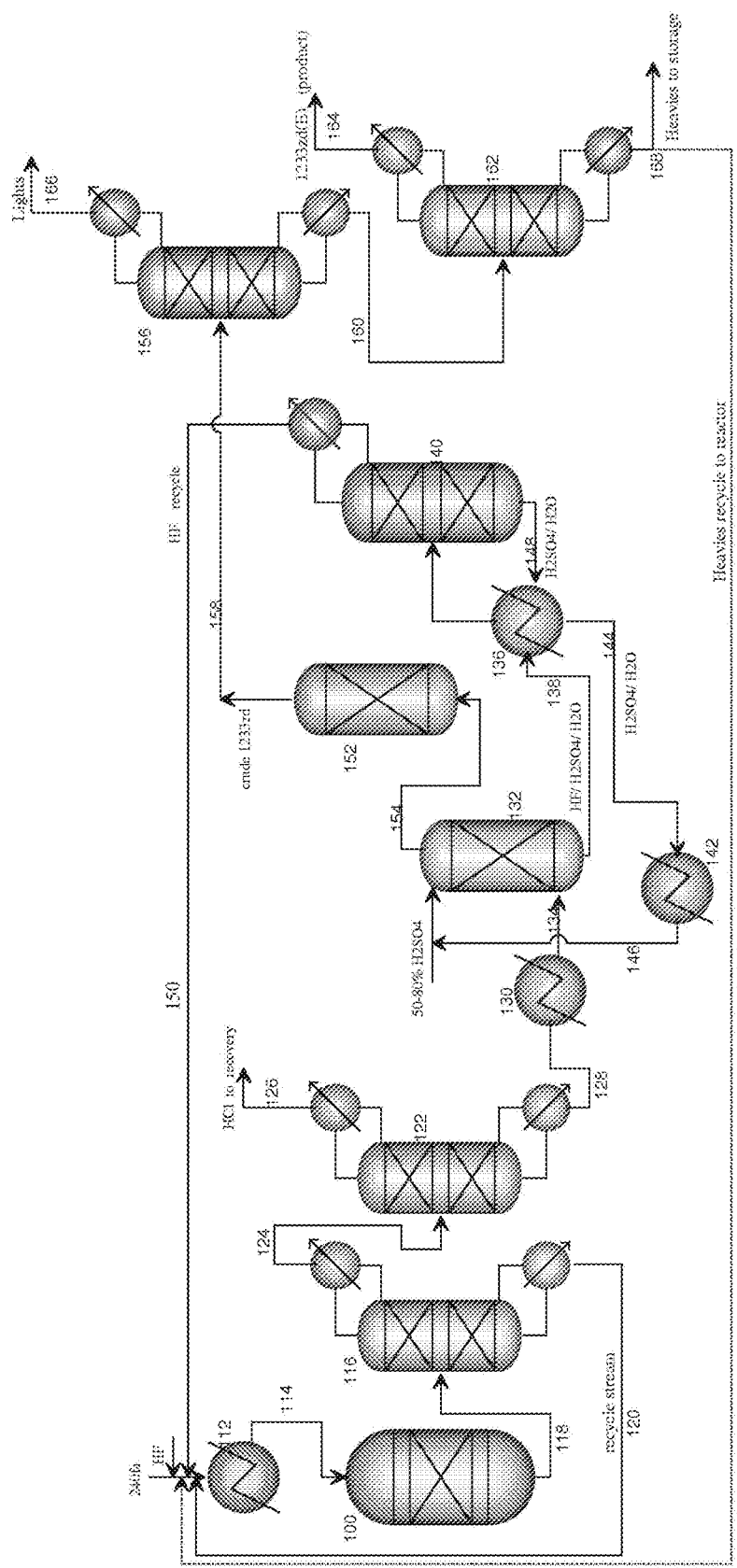
FIG. 6 is another schematic diagram of another vapor phase system that produces (E)1-chloro-3,3,3-trifluoropropene.

Referring to FIG. 6, shown is the synthesis of HCFO-1233zd(E) via a vapor phase reaction integrated process with sulfuric acid, HF recovery and optional recycle column after reactor. Specifically, a vapor phase reactor 100 is first loaded with a fluorination catalyst, as discussed above. Catalysts can be supported or in bulk, with preferred, though non-limiting catalysts, being fluorinated chromium oxide.

HCC-240fa and HF are simultaneously fed to a vaporizer 112 and then into a vapor phase reactor 100 via line 114. The reaction temperature may be about 200 to about 450° C. and at about 0 to about 160 psig pressure. The mole ratio of HF to HCC-240fa may be ≥3:1, preferably between 3:1 and 20:1, more preferably between 4:1 and 12:1, and most preferably between 5:1 and 11:1. The preferred catalyst in 100 is fluorinated chrome oxide.

The reactor effluent including partially fluorinated intermediates and by-products, overfluorinated by-products, HF, HCFO-1233zd(E+Z) and HCl, then enters recycle column 116 via line 118 where a stream 120 including mainly unreacted HCC-240fa, partially fluorinated intermediates, and the majority of the HF exits the bottom portion of the recycle column 116 and is recycled back to the vapor phase reactor 100 via vaporizer 112. A stream including mainly HCFO-1233zd(E), HF, and HCl exits the top portion of the recycle column and enters HCl column 122 via line 124. A stream 126 including mainly HCl by-product exits the top of the HCl column 122 and is fed to an HCl recovery system. The recovered HCl by-product can be used for other purposes, as discussed herein. The HCl column bottoms including mainly partially fluorinated by-products, overfluorinated by-products, HF and HCFO-1233zd(E+Z) are then fed into an HF recovery system via line 128.

The HF recovery system starts with the crude HCFO-1233zd/HF stream being vaporized in heat exchanger 130 and fed into HF absorption column 132. Here, a liquid stream of 50-80% $H_2SO_4$ contacts the gaseous HCFO-1233zd/HF stream and absorbs the majority of the HF. The stream exiting the bottom of column 132 includes $HF/H_2SO_4/H_2O$ and is fed to heat exchanger 136 via line 138 where it is heated to a temperature sufficient to flash the majority of the HF along with small amounts of $H_2O$ and $H_2SO_4$. This stream is fed to HF recovery distillation column 140. The liquid remaining after the HF is flashed off in heater exchanger 136 includes mainly $H_2SO_4$ and $H_2O$ (with 0-2% HF) and is cooled in heat exchanger 142 via line 144 and recycled back to HF absorption column 132 via line 146.

The HF recovery column 140 bottoms stream including mainly $H_2SO_4$ and $H_2O$ is recycled back to heat exchanger 136 via line 148. Anhydrous HF is recovered from the top portion of the HF recovery column 140, and is recycled back to the reactor 100 via line 150 and heat exchanger 112. The stream exiting the top of HF absorption column 132 including mainly HCFO-1233zd (E+Z) (trace HF) is sent forward via line 154 to a polishing system 152 where the gaseous stream contacts a water or a caustic solution to remove trace HF and is subsequently dried with a desiccant. Acid free crude product exiting absorber 152 is sent to the first of two purification columns 156 (and subsequently 162) via line 158. A stream 166 exiting the top portion of the column 156 includes mainly reaction by-products that have boiling points lower than that of HCFO-1233zd(E). The stream exiting the bottom portion of lights column 156 includes mainly HCFO-1233zd(E+Z) and heavier by-products is fed via line 160 to product recovery distillation column 162. Product grade HCFO-1233zd(E) exits the top portion of column 162 via line 164 to product storage. The product column bottoms 168 include mainly HCFO-1233zd (Z) and reaction by-products with boiling points higher than that of HCFO-1233zd(E) are then fed to vaporizer (not illustrated) and then to isomerization reactor (not illustrated) where by-product HCFO-1233zd (Z) is converted to the desired product. The stream leaving is then recycled to lights distillation column for purification. Optionally, if any by-products in the stream entering are unstable, they may decompose and form small amounts of HF or HCl. In this case, the stream exiting can be recycled and combined with the stream entering the polishing system to remove the acid. Optionally, the stream exiting the bottom portion of the product recovery distillation column can be recycled back to the vapor phase reactor where isomerization of Z to E isomer of HCFO-1233zd takes place. In any of these options, a heavies purge stream from the bottom of the product recovery distillation column prevents build-up of high boiling impurities in the purification system. The heavies purge stream is collected for later use or waste disposal. After deactivation of the catalyst in reactor 100, it can be regenerated in situ by heating to about 300 to about 400° C. and passing an oxidizing agent such as $O_2$ or over it for a selected period of time.

Figure 7:
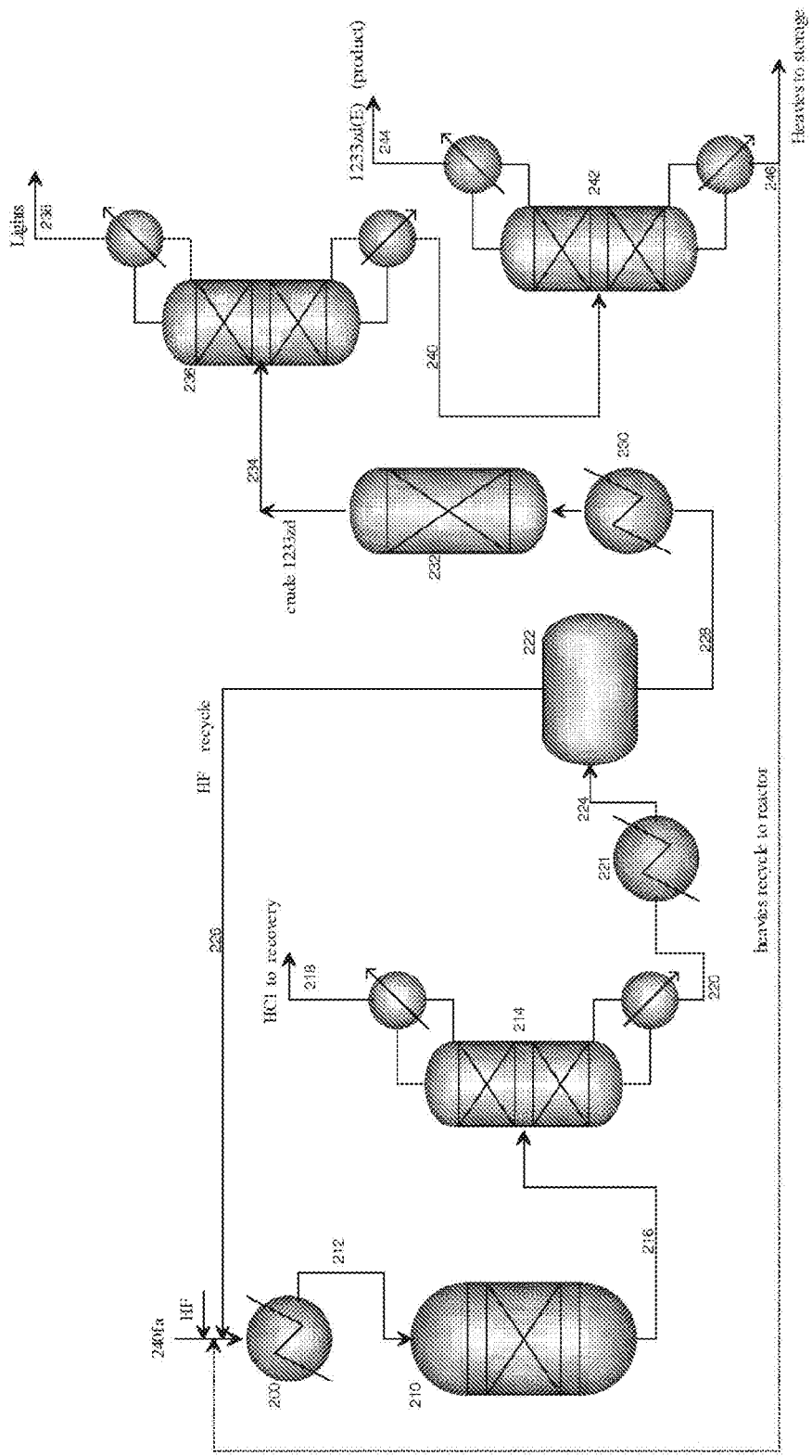
FIG. 7 is a further schematic diagram of a further vapor phase system that produces (E)1-chloro-3,3,3-trifluoropropene.

Referring to FIG. 7, shown is the synthesis of HCFO-1233zd (E) via a vapor phase reaction integrated process having a phase separation HF recovery system. Here, a vapor phase reactor 210 is first loaded with a fluorination catalyst, as discussed above. Catalysts can be supported or in bulk, with preferred, though non-limiting catalysts, being fluorinated chromium oxide.

HCC-240fa and HF are simultaneously fed to a vaporizer 200 and then into a vapor phase reactor 210 via line 212. The reaction temperature may be about 200 to about 450° C. and at about 0 to about 160 psig pressure. The mole ratio of HF to HCC-240fa is ≥3:1, preferably between 3:1 and 20:1, more preferably between 4:1 and 12:1, and most preferably between 5:1 and 11:1. The preferred catalyst in reactor 210 is fluorinated chrome oxide. The reactor effluent includes partially fluorinated intermediates and by-products, over-fluorinated by-products, overfluorinated by-products, HF, HCFO-1233zd(E+Z) and HCl, then enters HCl column 214 via line 216. A stream 218 including mainly HCl by-product exits the top portion of the HCl column 214 and is fed to an HCl recovery system (not shown) via line 218. The recovered HCl by-product can be used for other purposes, as discussed herein.

The HCl column bottoms consisting mainly of partially fluorinated intermediates and by-products, overfluorinated by-products, HF and HCFO-1233Z(E+Z) are then fed via line 220 into an HF recovery system. The HF recovery system starts with the HCFO-1233zd/HF stream being fed into heat exchanger 221 where it is pre-cooled to temperatures ≤0° C. and then enters phase separation vessel 222 via line 224. The stream temperature is maintained or further cooled to about −40 to about 0° C. The HF rich top layer (<10% 1233zd) is recycled via line 226 back to the vapor phase reactor 210. The organic rich bottom layer containing mainly HCFO-1233zd (<4% HF) is sent via line 228 to vaporizer 230 and the forward to a polishing system 232 where the gaseous stream contacts a water or a caustic solution to remove trace HF and is subsequently dried with a desiccant. Acid free crude product exiting absorber is sent via line 234 to the first of two purification columns 236. A stream 238 exiting the top portion of the column 236 includes mainly reaction by-products that have boiling points lower than that of HCFO-1233zd (E). The stream 240 exiting the bottom of lights column 236 including mainly HCFO-1233zd(E+Z) and heavier by-products is fed to product recovery distillation column 242. Product grade HCFO-1233zd(E) exits the top of the column 242 to product storage via line 244. The product column bottoms 246 include mainly HCFO-1233zd(Z) and reaction by-products with boiling points higher than that of HCFO-1233zd(E) is then fed to the vaporizer and then to the isomerization reactor where by-product HCFO-1233zd (Z) is converted to the desired product. The stream leaving is then recycled to the lights distillation column for purification. Optionally, if any by-products in the stream entering are unstable, they may decompose and form small amounts of HF or HCl. In this case, the stream exiting can be recycled and combined with the stream entering the polishing, system to remove the acid. Optionally, the stream exiting the bottom portion of the product recovery distillation column 242 can be recycled back to the vapor phase reactor where isomerization of Z to E isomer of HCFO-1233zd takes place. In any of these options, a heavies purge stream from the bottom portion of the product recovery distillation column prevents build-up of high boiling impurities in the purification system. The heavies purge stream is collected for later use or waste disposal. After deactivation of the catalyst in reactor 210 it can be regenerated in situ by heating to about 300 to about 400° C. and passing an oxidizing agent such as $O_2$ or $Cl_2$ over it for a prescribed period of time.

Figure 8:
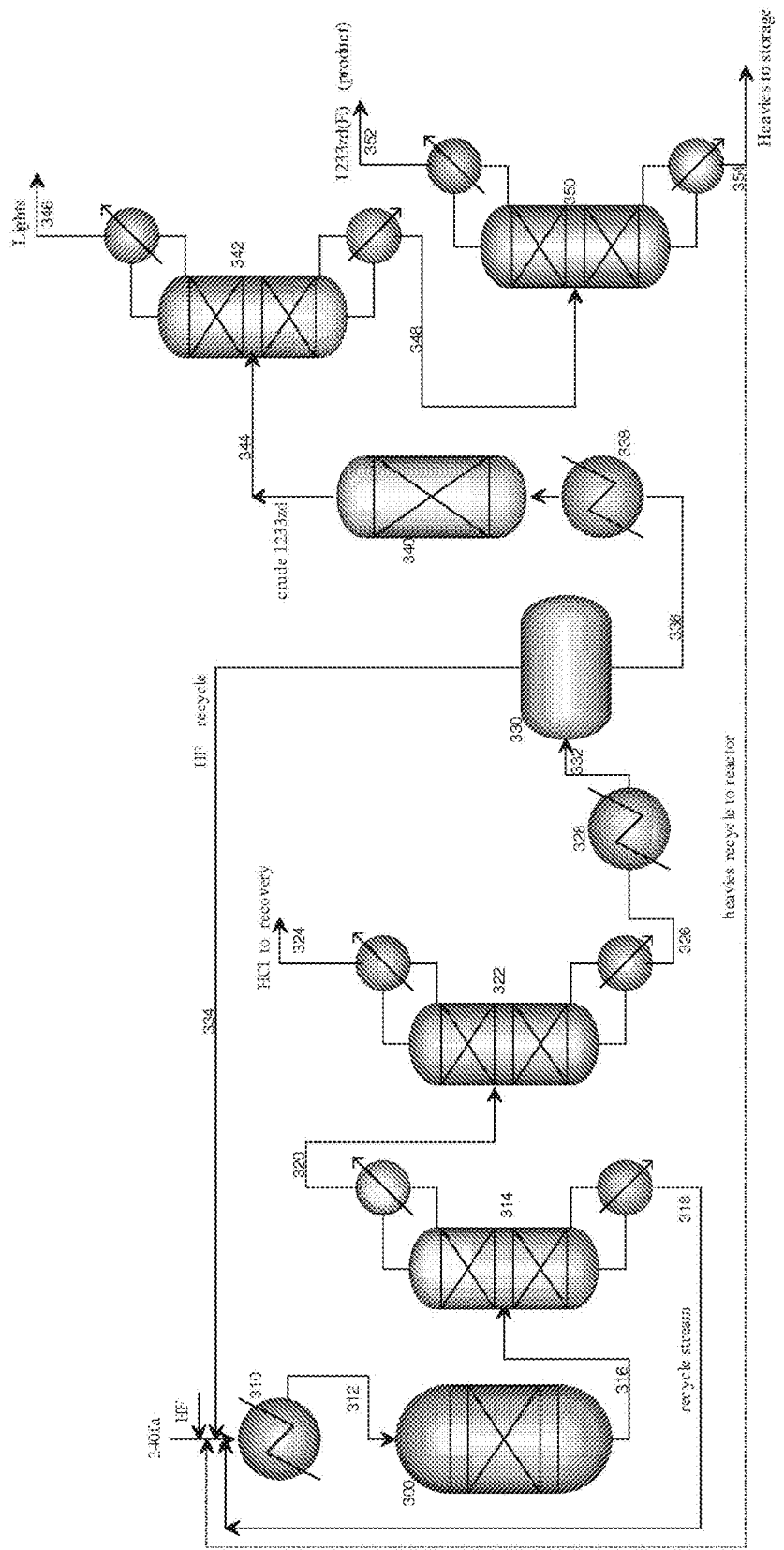
FIG. 8 is yet another schematic diagram of yet another vapor phase system that produces (E)1-chloro-3,3,3-trifluoropropene.

Referring to FIG. 8, shown is the synthesis of HCFO-1233zd (E) via a vapor phase reaction integrated process having a phase separation HF recovery system and optional recycle column after reactor. More specifically, a vapor phase reactor 300 is first loaded with a fluorination catalyst, as discussed above. Catalysts can be supported or in bulk, with preferred, though non-limiting catalysts, being fluorinated chromium oxide.

HCC-240fa and HF are simultaneously fed to a vaporizer 310 and then into vapor phase reactor 300 via line 312. The reaction temperature may be about 200 to about 450° C. and at about 0 to about 160 psig pressure. The mole ratio of HF to HCC-240fa is 3:1, preferably between 3:1 and 20:1, more preferably between 4:1 and 12:1, and most preferably between 5:1 and 11:1. The preferred catalyst in reactor 300 is fluorinated chrome oxide. The reactor effluent including partially fluorinated intermediates and by-products, overfluorinated by-products, HF, HCFO-1233zd (E+Z) and HCl, then enters recycle column 314 via line 316 where a stream including mainly unreacted HCC-240fa, partially fluorinated intermediates, and the majority of the HF exits the bottom portion of recycle column 314 and is recycled back to the vapor phase reactor 300 via line 318 and vaporizer 310. A stream including mainly HCFO-1233zd (E), HF and HCl exits the top portion of the recycle column 314 via line 320 and enters HCl column 322. A stream 324 including mainly HCl by-product exits the top portion of HCl column 322 and is fed to an HCl recovery system (not shown). The recovered HCl by-product can be used for other purposes, as discussed herein. The HCl column bottoms including mainly partially fluorinated by products, overfluorinated by-products, HF and HCFO-1233zd (E+Z) are then fed via line 326 into an HF recovery system.

The HF recovery system starts with the HCFO-1233zd/HF stream being fed into heat exchanger 328 where it is pre-cooled to temperatures ≤0° C. and then enters phase separation vessel 330 via line 332. The stream temperature may be maintained or further cooled to about −40 to about 0° C. The HF rich top layer (<10% 1233zd) may be recycled back to the vapor phase reactor 300 via line 334. The organic rich bottom layer containing mainly HCFO-1233zd (<4% HF) is sent via line 336 to vaporizer 338 and then forwarded to a polishing system 340 where the gaseous stream contacts a water or a caustic solution to remove trace HF and is subsequently dried with a desiccant.

Acid free crude product exiting absorber 340 is sent to the first of two purification columns, 342 via line 344. A stream 346 exiting the top of the column 342 includes mainly reaction by-products that have boiling points lower than that of HCFO-1233zd(E). The stream 348 exiting the bottom portion of lights column 342 including mainly HCFO-1233zd (E+Z) and heavier by-products is fed to product recovery distillation column 350. Product grade HCFO-1233zd(E) exits the top of the column to product storage via line 352. The product column bottoms 354 include mainly HCFO-1233zd(Z) and reaction by-products with boiling points higher than that of HCFO-1233zd(E) are then fed to the vaporizer (not illustrated) and then to the isomerization reactor (not illustrated) where by-product HCFO-1233zd(Z) is converted to the desired product. The stream leaving is then recycled to the lights distillation column for purification. Optionally, if by-products in the stream entering are unstable, they may decompose and form small amounts of HF or HCl. In this case, the stream exiting can be recycled and combined with the stream entering the polishing system to remove the acid. Optionally, the stream exiting the bottom portion of the product recovery distillation column can be recycled back to the vapor phase reactor where isomerization of Z to E isomer of HCFO-1233zd takes place. In any of these options, a heavies purge stream from the bottom portion of the product recovery distillation column prevents build-up of high boiling impurities in the purification system. The heavies purge stream is collected for other use or waste disposal. After deactivation of the catalyst in reactor 300 it can be regenerated in situ by heating to about 300 to about 400° C. and passing an oxidizing agent such as $O_2$ or $Cl_2$ over it for a selected period of time.

Specific embodiments of the present invention will now be described in the following Examples. The Examples are illustrative only, and are not intended to limit the remainder of the disclosure in any way.

EXAMPLES

Example 1

This example (called Run #3) illustrates the semi-batch, liquid phase, reaction where HF was continuously fed into a charge of Titanium tetrachloride catalyst and 1,1,1,3,3-pentachloropropane (HCC-240fa).

A clean, empty 10-gallon jacketed, agitated reactor of Hastelloy C construction was prepared. This reactor was connected to a 2" vertical, PTFE-lined pipe containing packing material (stripper), which was in turn connected to an overhead heat exchanger. The heat exchanger was supplied with −40° C. brine circulation on the shell side. Vapors exiting this stripper were processed through a scrubber, in which temperature-controlled dilute potassium hydroxide aqueous solution was circulated. Vapors exiting this stripper were collected in a weighed, chilled (−40° C.) cylinder referred to as the product collection cylinder, followed by a smaller cylinder in series chilled in a dry ice bath.

For Run #3, 14 lbs. of anhydrous HF was fed to assure catalyst fluorination. Next, 1.5 lbs. of $TiCl_4$ was added as a catalyst. HCl was immediately generated as observed by the build-up of pressure in the reactor. After the pressure was reduced by venting most of the HCl from the system, 50 lbs. of HCC-240fa was added. The reactor was heated. At about 85° C. HCl started to be generated indicating that the fluorination reaction was initiated. The system pressure was controlled at about 120 psig. Additional HF was then fed continuously and product was collected in the product collection cylinder until the HCC-240fa was consumed.

The GC analysis of the crude material collected during the run was as follows:

TABLE 1

| Wt. Percent | Compound |
| --- | --- |
| 86.4% | 1233zd(E) |
| 5.5% | G-244fa |
| 3.1% | 1234ze(E) |
| 1.5% | 1233zd(Z) |
| 1.1% | 1234ze(Z) |
| 1.1% | dimer |
| 0.2% | trifluoropropyne |

Example 2

Following Run #3 from Example 1, the reactor was drained, and a fresh charge of catalyst was made, and Run #4 was performed in a similar manner to Run #3.

The catalyst charge for Run #4 was 753 grams of $TiCl_4$. The operating scheme for this run continued the same as Run #3—an initial batch charge of 14.3 lbs of HF was added before the catalyst. Then HCC-240fa (51.9 lbs) was added on top of the catalyst after HCl from the fluorination of the catalyst was complete. After the reaction temperature was achieved, continuous HF feed was started and maintained until either the analysis of the product quality showed a dramatic drop, or the collection of product weight subsided—at these times, a fresh charge of HCC-240fa was made (typically 25-30 lbs.) and continuous HF feed was resumed.

Catalyst productivity for Run #4 was approximately 0.4 pph/lb of catalyst. About 244 lbs of crude 1233zd(E) was collected during the run.

The run was continued for over 900 hours without loss of catalyst activity.

Example 3

This example illustrates a continuous liquid phase fluorination reaction where HF and an organic feed mixture of 1,1,1,3,3-pentachloropropane, 1,1,3,3-tetrachloropropene, and 1,3,3,3-tetrachloropropene is continuously fed into a charge of Titanium tetrachloride catalyst.

The same 10-gallon jacketed reactor system from Examples 1 and 2 is used.

30 lbs. of anhydrous HF is charged to the reactor. This amount is in excess of that needed to fluorinate the TiCl4 catalyst. The agitator is started at 250 RMPs. Next, 1.5 lbs. of $TiCl_4$ is added as a catalyst. HCl is immediately generated as observed by the build-up of pressure in the reactor. After the pressure is reduced by venting most of the HCl from the system, 20 lbs. of an organic feed mixture consisting of 70 wt % 1,1,1,3,3-pentachloropropane, 27 wt % 1,1,3,3-tetrachloropropene, and 3 wt % 1,3,3,3-tetrachloropropene is added. The reactor is then heated by adding steam to the jacket. At about 85° C. HCl starts to be generated indicating that the fluorination reaction has been initiated. The system pressure is then controlled at about 120 psig. Additional HF and organic feed mixture is then fed continuously at a mole ratio of 9:1 HF to organic. A stream consisting mainly of HCl by-product, 1233zd, and excess HF is vented off the top of the catstripper, scrubbed to remove acid, and organic collected in the product collection cylinder.

The GC analysis of the crude material collected during the run was as follows:

TABLE 2

| Wt. Percent | Compound |
| --- | --- |
| 94% | 1233zd(E) |
| 3.2% | G-244fa |
| 1.4% | 1234ze(E) |
| 0.5% | 1233zd(Z) |
| 0.5% | others |

Example 4

This example illustrates the recovery of anhydrous HF from a mixture of HF and HCFO-1233zd according to certain preferred embodiments of the present invention.

A mixture consisting of about 70 wt. % HCFO-1233zd (E) crude and about 30 wt. % HF is vaporized and fed to the bottom of a packed column at a feed rate of about 2.9 lbs per hour for about 4 hours. A stream of about 80 wt. % sulfuric acid (80/20 $H_2SO_4/H_2O$) with about 2% HF dissolved therein is fed continuously to the top of the same packed column at a feed rate of about 5.6 lbs per hour during the same time frame. A gaseous stream exiting the top of the column comprises HCFO-1233zd (E) crude with less than 1.0 wt. % HF therein. The concentration of HF in the sulfuric acid in the column bottoms increases from 2.0 wt. % to about 15 wt. %.

The column bottoms containing sulfuric acid and about 15 wt. % HF is collected and charged into a 2 gallon teflon vessel. The mixture is heated to about 140° C. to vaporize and flash off HF product, which is collected. The collected HF product contains about 6000 ppm water and 500 ppm sulfur. The sulfuric acid contains about 500 ppm of TOC (total organic carbon).

The HF collected from flash distillation is distilled in a fractionation distillation column and anhydrous HF is recovered. The recovered anhydrous HF contains less than 50 ppm of sulfur impurities and less than 100 ppm water.

Example 5

This example demonstrates the purification of the acid free 1233zd(E) crude product.

About 92 lbs of acid free 1233zd crude material produced in Example 2 was charged to a batch distillation column. The crude material contained about 94 GC area % 1233zd(E) and 6 GC area % impurities. The distillation column consisted of a 10 gallon reboiler, 2 inch ID by 10 feet propack column, and a shell and tube condenser. The column had about 30 theoretical plates. The distillation column was equipped with temperature, pressure, and differential pressure transmitters. About 7 lbs of a lights cut was recovered which consisted of mainly 1234ze(Z+E), trifluoropropyne, 245fa, and 1233zd(E). 82 lbs of 99.8+GC area % 1233zd(E) were collected. The reboiler residue amounting to about 3 lbs was mainly 244fa, 1233zd(Z), 1233zd dimmer, and 1233zd(E). The recovery of 99.8+GC area % pure 1233zd(E) was 94.8%.

Example 6

This example demonstrates the purification of the acid free 1233zd(E) crude product. About 92 lbs of acid free 1233zd crude material produced in Example 2 was charged to a batch distillation column. The crude material contained about 94 GC area % 1233zd(E) and 6 GC area % impurities. The distillation column consisted of a 10 gallon reboiler, 2 inch ID by 10 feet propack column, and a shell and tube condenser. The column had about 30 theoretical plates. The distillation column was equipped with temperature, pressure, and differential pressure transmitters. About 7 lbs of a lights cut was recovered which consisted of mainly 1234ze (Z+E), trifluoropropyne, 245fa, and 1233zd(E). 82 lbs of 99.8+GC area % 1233zd(E) were collected. The reboiler residue amounting to about 3 lbs was mainly 244fa, 1233zd (Z), 1233zd dimmer, and 1233zd(E). The recovery of 99.8+ GC area % pure 1233zd(E) was 94.8%.

Example 7

This example demonstrates the use of the optional recycle column.

A representative 1233zd(E) liquid phase reactor effluent mixture as determined in Example 2 is charged into a batch distillation column. The distillation column consists of a 10 gallon reboiler, 2 inch ID by 10 feet propack column, and a shell and tube condenser with −40° C. coolant flow capability. The column has about 30 theoretical plates. The distillation column is equipped with temperature, pressure, and differential pressure transmitters. The distillation column feed mixture is about 30 wt % HF, 37 wt % HCl and 33% 1233zd(E) crude. The distillation is run at a pressure of about 100 psig and a differential pressure (delta P) of 15-20 inches of water. Both the distillate and reboiler are sampled periodically and analyzed for organic, HF, and HCl using gas and ion Chromatography. Initially, HCl, organic, and HF are observed in both samples. As more material is removed as distillate the concentration of the reboiler changes. First, the concentration of HCl decreases until it is undetectable. The distillation is allowed to proceed until the concentration of organic in the reboiler sample decreases to only trace amounts as analyzed using gas chromatography. At the conclusion of the distillation the material remaining in the reboiler is essentially pure HF. The recovered HF (reboiler bottoms) is then used to demonstrate recycle of recovered HF back to the liquid phase fluorination reactor and works satisfactorily.

Example 8

This example demonstrates the HF recovery by phase separation.

It is visually observed using a Teflon cylinder that HF and 1233zd(E) form a heterogeneous mixture. The separation of 1233zd and HF layers is tested in the temperature range from +10° C. to −30° C. The phase-separation of a mixture containing 1233zd(E) and HF is performed in the temperature range of −30° C. to +10° C. A 500 ml SS sample cylinder is used for the study. The temperature of the cylinder is controlled with ethanol circulating through the coil wrapped around the cylinder. A thermocouple is attached to the outside wall of the cylinder (between cooling coil and the cylinder wall) and positioned in the middle of the cylinder to measure the temperature. The cylinder is also equipped with sampling valves at the bottom and the top of the cylinder. To the cylinder is charged 100 g of anhydrous HF and 250 g of a 1233zd(E). The weight ratio HF:1233zd (E) is 28.6:71.4. The cylinder is padded with nitrogen to 15 psig at −30° C. to allow sampling. Samples are taken from the bottom of the cylinder into Tedlar gas sample bags that contains 5 grams of distilled water for the purpose of absorbing HF. The first sample is taken two hours after the cylinder reaches the desired temperature. HF concentration is determined by titration with 0.1 N KOH of the aqueous phase of the sample bags. HF concentration in samples taken after 2 hours at given temperature is presented in Table 3.

HF concentration in the HF layer is analyzed after the organic layer was removed from the system. KOH titration showed that concentration of HF in the acid layer was about 70±5%.

TABLE 3

HF concentration in the samples of the bottom (organic) phase taken after equilibrating the contents of the phase-separator for 2 hours at given temperature

| Temperature (° C.) | HF concentration in bottom (organic phase (wt %) |
| --- | --- |
| −30 | 1.00 |
| −20 | 1.25 |
| −10 | 2.75 |
| 0 | 3.25 |
| 10 | 4.00 |

Example 9

This example demonstrates the isomerization of 1233zd (Z) into desired product 1233zd (E).

Conversion of 1233zd(Z) into 1233zd(E) was performed using a MONEL™ reactor (ID 2 inch, length 32 inch) equipped with a MONEL™ preheater (ID 1 inch, length 32 inch) which was filled with Nickel mesh to enhance heat transfer. The reactor was filled with 1.5 L of pelletized fluorinated $Cr_2O_3$ catalyst. Nickel mesh was placed at the top and at the bottom of reactor to support the catalyst. A multi-point thermocouple was inserted at the center of the reactor. A feed containing about 10.0 wt % 1233zd(E) and 86.3 wt % 1233zd(Z) was introduced into the reactor at the rate of 0.7 lb/hr. The feed was vaporized prior to entering the reactor preheater. The reactor temperature for this experiment was varied between 100° C. and 200° C. The temperature gradient throughout the reactor never exceeded 3-5° C. Samples of reaction products were taken every hour and GC analysis of those samples is given in Table 4.

TABLE 4

| Reaction Temp. | Area Percent by GC | | |
| --- | --- | --- | --- |
| ° C. | 1233zd(E) | 1233zd(Z) | Others |
| Initial | 10.0 | 86.3 | 3.7 |
| 103 | 69.6 | 27.9 | 2.5 |
| 104 | 69.8 | 27.9 | 2.4 |
| 128 | 70.2 | 27.6 | 2.2 |
| 128 | 65.0 | 32.8 | 2.2 |
| 128 | 62.8 | 35.0 | 2.2 |
| 128 | 60.9 | 36.9 | 2.2 |
| 151 | 60.8 | 37.1 | 2.1 |
| 151 | 61.8 | 36.2 | 2.0 |
| 151 | 62.4 | 35.6 | 2.0 |
| 151 | 58.9 | 39.0 | 2.1 |
| 181 | 62.2 | 35.8 | 2.0 |
| 199 | 68.3 | 29.4 | 2.3 |

Example 10

This example illustrates a continuous vapor phase fluorination reaction of 1,1,1,3,3-pentachloropropane (HCC-240fa)+3HF→1-chloro-3,3,3-trifluoropropene (1233zd)+4HCl. The fluorination catalyst for the experiment was fluorinated $Cr_2O_3$.

A continuous vapor phase fluorination reaction system including $N_2$, HF, and organic feed systems, feed vaporizer, superheater, 2" ID monel reactor, acid scrubber, dryer, and product collection system was used to study the reaction. The reactor wad loaded with 2135 grams of fluorinated $Cr_2O_3$ catalyst which is about 1.44 liters of catalyst. The reactor was then heated to a reaction temperature of about 275° C. with a $N_2$ purge over the catalyst after the reactor had been installed in a constant temperature sand bath. The reactor was maintained at about 2 psig of pressure. HF feed was introduced to the reactor (via the vaporizer and superheater) as a co-feed with N, for 15 minutes when the $N_2$ flow was stopped. The HF flow rate was adjusted to 1.0 lb/hr and then 1,1,1,3,3-pentachloropropane (HCC-240fa) feed was introduced in to the reactor (via the vaporizer and superheater). The feed rate of HCC-240fa was kept steady at about L2 lb/hr and HF feed was kept steady at 1.0 lb/hr for about a 9 to 1 mole ratio of HF to 240fa. Once the reaction started, the catalyst bed temperature was adjusted to about 328 to about 332° C. The average composition of the material at the exit of the reactor was about 83.0 GC area % HCFO-1233zd(E), 8.95 GC area % HCFO-1233zd (Z), 3.48 GC area % 1234ze(E), 2.06 GC area % 245fa, 1.41 GC area % 1234ze(Z), and 0.08 GC area % 3,3,3-trifluoropropyne. During about 200 hours on stream, the position of a hot spot inside the catalyst bed moved from the inlet to the exit section of the reactor indicating partial deactivation of the catalyst, but the conversion of 240fa was remained at 100% throughout the run.

Example 11

The fluorinated $Cr_2O_3$ catalyst deactivated after 200 hours of on-stream time as described in Example 10 was regenerated by the following procedure:

The reactor was heated to 300° C. while flowing $N_2$ at a rate of 5000 cc/min.

Synthetic air was introduced after reactor temperatures stabilized. Air flow was started with a rate that gave 0.5% $O_2$. Gradually, with 0.25% $O_2$ increments, air flow was increased to achieve $O_2$ concentration of 2.0%. Then, reactor hot-spot was brought to 360° C. and the air flow rate was gradually, in 0.5-1.0% increments, increased to achieve $O_2$ concentration of 5.0%. Careful adjustments of reactor heater temperature were needed to avoid overheating the reactor above 380° C.

The reactor was maintained at a 360-375° C. hot spot temperature while flowing 5% $O_2/N_2$ until the hot spot reached the top of the catalyst bed. Then, without changing reactor heater temperature, $O_2$ flow was maintained until the reactor temperature approached that of the reactor heater. Then, the reactor was purged with $N_2$ for 5 hours to remove residual oxygen and moisture. That completed the regeneration of the catalyst and the reactor was brought to 275° C. to prepare it for re-fluorination with HF.

The 240fa+3HF→1233zd+4HCl reaction was restarted at the same operating conditions described in Example 10. The position of the hot-spot moved back to the inlet of the reactor. The conversion of 240fa was about 100%.

Example 12

This example is similar to Example 10 except that reactor temperature was varied between 310° C. and 350° C., reaction pressure was varied between 2 psig and 25 psig, 240fa feed rate was kept constant at 1.2 lb/hr and HF feed was varied to achieve HF:240fa molar ratio between 6.3 and 9. The effects of the reaction conditions are presented in Table 5.

TABLE 5

| HF: 240fa Mole ratio | Pressure psig | Temp. ° C. | t-1234ze GC. % | c-1234ze GC. % | 245fa GC. % | t-1233zd GC. % | c-1233zd GC. % |
|---|---|---|---|---|---|---|---|
| 9.0 | 25 | 310 | 3.0915 | 0.7932 | 6.0226 | 78.8773 | 8.8861 |
| 9.0 | 2 | 310 | 3.3722 | 0.9808 | 3.3337 | 80.8924 | 8.6707 |
| 9.0 | 25 | 350 | 4.1646 | 1.0482 | 3.1154 | 80.4220 | 9.3069 |
| 9.0 | 2 | 350 | 3.9863 | 1.1476 | 1.4706 | 82.0814 | 9.7896 |
| 6.3 | 2 | 350 | 2.1189 | 0.6183 | 0.7510 | 85.1545 | 9.4874 |
| 6.3 | 25 | 310 | 1.7233 | 0.4568 | 2.6915 | 84.3689 | 8.9174 |
| 6.3 | 2 | 310 | 1.8676 | 0.5473 | 1.4649 | 85.6759 | 9.0857 |
| 6.3 | 25 | 350 | 2.2432 | 0.6582 | 1.6793 | 83.9624 | 9.5061 |

Example 13

This example illustrates purification of the target product HCFO-1233zd(E).

A distillation column was charged with 118.9 lb of the acid free crude HCFO-1233zd product. The composition of the crude mixture is shown in Table 6.

TABLE 6

Composition of crude HCFO-1233zd product charged in to the distillation column

| Component | Conc. (GC %) |
|---|---|
| $CF_3CCH$ | 3.74 |
| 1234ze(E) | 7.65 |
| 1234ze(Z) | 1.06 |
| 245fa | 1.75 |
| 1233xf | 0.11 |
| 1233zd(E) | 81.38 |
| 1233zd(Z) | 4.08 |
| others | 0.23 |

The distillation column consisted of a 10-gallon reboiler, 2-inch ID by 10 feet long column packed with Propack high efficiency distillation column packing, and a shell and tube condenser. The column had about 30 theoretical plates. The distillation column was equipped with temperature, pressure, and differential pressure transmitters. The distillation was run at a pressure of about 40-50 psig during the lights cut and at a pressure of about 30 psig during the main, HCFO-1233zd(E), cut. The distillate was sampled and analyzed by GC at regular intervals. Two separate cuts were collected: lights cut and main cut. Hiboilers were drained from the bottom of the reboiler after the distillation was complete. The recovery of essentially pure HCFO-1233zd (E) was about 76%. The compositions and weights of three cuts are listed in Table 7.

TABLE 7

Composition of the distillation cuts collected during the distillation described in the Example 13.

| Component | 1233zd(E) cut 73.8 lb Concentration (GC %) | LIGHTS 38.3 lb Concentration (GC %) | BOTTOMS 6.8 lb Concentration (GC %) |
|---|---|---|---|
| $CF_3CCH$ | — | 11.6 | — |
| 1234ze(E) | — | 23.75 | — |
| 1234ze(Z) | — | 3.3 | — |
| 245fa | — | 5.44 | — |
| 1233xf | — | 0.35 | — |
| 1233zd(E) | >99.99 | 55.29 | 26.18 |
| 1233zd(Z) | — | — | 71.29 |
| Others | — | 0.27 | 2.53 |

Example 14

This example illustrates the recovery of anhydrous HF from a mixture of HF and HCFO-1233zd.

A mixture consisting of about 70 wt. % trans-HCFO1233zd and about 30 wt. % HF is vaporized and fed to the bottom of a packed column at a feed rate of about 2.9 lbs per hour for about 4 hours. A stream of about 80 wt. % sulfuric acid (80/20 $H_2SO_4/H_2O$) with about 2% HF dissolved therein is fed continuously to the top of the same packed column at a feed rate of about 5.6 lbs per hour during the same time frame. A gaseous stream exiting the top of the column comprises trans-HCFO1233zd with less than 1.0 wt. % HF therein. The concentration of HF in the sulfuric acid in the column bottoms increases from 2.0 wt. % to about 15 wt. %.

The column bottoms containing sulfuric acid and about 15 wt. % HF is collected and charged into a 2-gallon Teflon vessel. The mixture is heated to about 140° C. to vaporize and flash off HF product, which is collected. The collected HF product contains about 6000 ppm water and 500 ppm sulfur.

The HF collected from flash distillation is distilled in a distillation column and anhydrous HF is recovered. The recovered anhydrous HF contains less than 50 ppm of sulfur impurities and less than 100 ppm water.

Example 15

This example demonstrates the use of the recycle column.

A representative HCFO-1233zd vapor phase reactor effluent mixture as determined in Examples 10 and 11 is charged into a batch distillation column. The distillation column includes a 10-gallon reboiler, 2-inch ID by 10 feet long column packed with Propack high efficiency distillation column packing, and a shell and tube condenser with −40° C. coolant flow capability. The column has about 30 theoretical plates. The distillation column is equipped with temperature, pressure, and differential pressure transmitters. The distillation column feed mixture is about 30 wt. % HF, 37 wt. % HCl and 33% HCFO-1233zd (E) crude. The distillation is run at a pressure of about 100 psig and a differential pressure (delta P) of 15-20 inches of water. Both the distillate and reboiler are sampled periodically and analyzed for organic, HF, and HCl using gas and ion chromatography. Initially, HCl, organic and HF are observed in both samples. As more material is removed as distillate the concentration of the reboiler changes. First, the concentration of HCl decreases until it is undetectable. The distillation proceeds until the concentration of organic in the reboiler sample decreases to only trace amounts as analyzed using gas chromatography. The material remaining in the reboiler at the conclusion of the distillation is essentially pure HF. The recovered HF (reboiler bottoms) is then used to demonstrate recycle of recovered HF back to the vapor phase fluorination reactor and works satisfactorily.

Example 16

This example demonstrates the HF recovery by phase separation.

It is visually observed using a Teflon cylinder that HF and HCFO-1233zd form a heterogeneous mixture. The separation of HCFO-1233zd and HF layer is tested in the temperature range from +10° C. to −30° C.

The phase-separation of a mixture containing HCFO-1233zd and HF is performed in the temperature range of −30° C. to +10° C. A 500 ml SS sample cylinder is used. The temperature of the cylinder is controlled with ethanol circulating through the coil wrapped around the cylinder. A thermocouple is attached to the outside wall of the cylinder (between cooling coil and the cylinder wall) and positioned in the middle of the cylinder to measure the temperature. The cylinder is also equipped with sampling valves at the bottom and the top of the cylinder. To the cylinder is charged 100 g of anhydrous HF and 250 g of HCFO-1233zd (E). The weight ratio HF:HCFO-1233zd (E) is 28.6:71.4. The cylinder is padded with nitrogen to 15 psig at −30° C. to allow sampling. Samples are taken from the bottom of the cylinder into Tedlar gas sample bags that contain 5 grams of distilled water for the purpose of absorbing HF. The first sample is taken two hours after the cylinder reaches the desired temperature. HF concentration is determined by titration with 0.1 N KOH of the aqueous phase of the sample bags. HF concentration in samples taken after 2 hours at given temperature is presented in Table 8.

HF concentration in the HF layer is analyzed after the organic layer was removed from the system. KOH titration showed that concentration of HF in the acid layer was about 70±5%.

TABLE 8

HF concentration in the samples of the bottom (organic) phase taken after equilibrating the contents of the phase-separator for 2 hours at given temperature

| Temperature (° C.) | HF concentration in bottom (organic) phase (wt. %) |
| --- | --- |
| −30 | 1.00 |
| −20 | 1.25 |
| −10 | 2.75 |
| 0 | 3.25 |
| 10 | 4.00 |

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claim.

What is claimed is:

1. An integrated system for producing a hydrofluoroolefin comprising:
   a. one or more feed streams cumulatively comprising hydrogen fluoride and one or more hydrohalocarbons selected from the group consisting of 1,1,1,3,3-pentachloropropane, 1,1,3,3-tetrachloropropene, 1,3,3,3-tetrachloropropene, and combinations thereof;
   b. a liquid phase reactor charged with a liquid phase fluorination catalyst and maintained at a first temperature of about 85° C. to about 120° C., wherein said liquid phase reactor is fluidly connected to said one or more feed streams and wherein said liquid phase fluorination catalyst is selected from the group consisting of partially or fully fluorinated TiCl4, SnCl4, TaCl5, SbCl3, FeCl3, or AlCl3;
   c. a stripping system comprising a stripping column having an average temperature maintained at a second temperature of about 10° C. to about 40° C. below said first temperature, a reflux stream fluidly connected to said stripping column, and a first crude product stream fluidly connected to said stripping column, wherein said reflux stream is fluidly connected to said liquid phase reactor;
   d. a hydrogen chloride removal system comprising a first distillation column, a hydrogen chloride by-product stream fluidly connected to said first distillation column, and a second crude product stream fluidly connected to said first distillation column, wherein said first distillation column is fluidly connected to said stripping column;
   e. a hydrogen fluoride recovery system comprising a sulfuric acid stripping and recycle system or a phase separation vessel, a second recycle stream comprising hydrogen fluoride fluidly connected to said sulfuric acid stripping and recycle system or a phase separation vessel, a third product stream comprising (E) and (Z) 1-chloro-3,3,3-trifluoropropene fluidly connected to said sulfuric acid stripping and recycle system or a phase separation vessel, wherein said sulfuric acid stripping and recycle system or a phase separation vessel is fluidly connected to said second crude product stream;
   f. a 1-chloro-3,3,3-trifluoropropene purification system comprising a second distillation column fluidly connected to said third product stream;
   a final product stream comprising (E) 1-chloro-3,3,3-trifluoropropene fluidly connected to said second distillation column;
   a second by-product stream fluidly connected to said distillation column,
   an isomerization reactor fluidly connected to said second by-product stream; and
   a product recycle stream fluidly connected to said isomerization reactor and said second distillation column.

2. An integrated system for producing a hydrofluoroolefin comprising:
   a. one or more feed streams cumulatively comprising hydrogen fluoride and 1,1,1,3,3-pentachloropropane;

b. a vapor phase reactor with a vapor phase fluorination catalyst and maintained at a first temperature of about 200 to about 450° C. and a pressure of about 0 to about 160 psig, wherein said vapor phase reactor is fluidly connected to said one or more feed streams;

c. a hydrogen chloride removal system comprising a first distillation column, a hydrogen chloride by-product stream fluidly connected to said first distillation column, and a crude product stream fluidly connected to said first distillation column wherein said first distillation column is fluidly connected to said vapor phase reactor;

d. a hydrogen fluoride recovery system comprising a sulfuric acid stripping and recycle system or a phase separation vessel, a recycle stream comprising hydrogen fluoride fluidly connected to said sulfuric acid stripping and recycle system or a phase separation vessel, a product stream comprising (E) and (Z) 1-chloro-3,3,3-trifluoropropene fluidly connected to said sulfuric acid stripping and recycle system or a phase separation vessel, wherein said sulfuric acid stripping and recycle system or a phase separation vessel is fluidly connected to said crude product stream;

e. a 1-chloro-3,3,3-trifluoropropene purification system comprising a second distillation column fluidly connected to said product stream;

a final product stream comprising (E) 1-chloro-3,3,3-trifluoropropene fluidly connected to said second distillation column;

a second by-product stream fluidly connected to said distillation column, an isomerization reactor fluidly connected to said second by-product stream; and a product recycle stream fluidly connected to said isomerization reactor and said second distillation column.

\* \* \* \* \*